(12) United States Patent
Kashimura et al.

(10) Patent No.: US 12,073,964 B2
(45) Date of Patent: Aug. 27, 2024

(54) LAMINATE STRUCTURE, CABLE AND TUBE

(71) Applicant: Hitachi Metals, Ltd., Tokyo (JP)

(72) Inventors: Seiichi Kashimura, Tokyo (JP); Kazufumi Suenaga, Tokyo (JP); Tamotsu Kibe, Tokyo (JP); Kanako Suganuma, Tokyo (JP)

(73) Assignee: Proterial, Ltd., Tokyo (JP)

( * ) Notice: Subject to any disclaimer, the term of this patent is extended or adjusted under 35 U.S.C. 154(b) by 0 days.

(21) Appl. No.: 17/666,190

(22) Filed: Feb. 7, 2022

(65) Prior Publication Data

US 2022/0254543 A1     Aug. 11, 2022

(30) Foreign Application Priority Data

Feb. 9, 2021   (JP) ................................. 2021-019099
Jun. 11, 2021   (JP) ................................. 2021-098350

(51) Int. Cl.
    *H01B 7/17*            (2006.01)
    *C09D 5/32*            (2006.01)
    (Continued)

(52) U.S. Cl.
    CPC ................. *H01B 7/17* (2013.01); *C09D 5/32* (2013.01); *C09D 7/61* (2018.01); *C09D 183/00* (2013.01)

(58) Field of Classification Search
    CPC ... B32B 1/08; B32B 2250/248; B32B 25/042; B32B 25/20; B32B 2255/02;
    (Continued)

(56) References Cited

U.S. PATENT DOCUMENTS 3,862,082 A *   1/1975   Hatanaka ............... C08K 3/016
                                                      524/588
4,061,503 A *   12/1977   Berger .................. C09C 1/3684
                                                      106/445

(Continued)

FOREIGN PATENT DOCUMENTS

CN          109762338 A      5/2019
JP          09194730 A *      7/1997

(Continued)

OTHER PUBLICATIONS

Extended European Search Report issued in the corresponding EP Application No. 22155577.4 dated Jun. 13, 2022.

(Continued)

*Primary Examiner* — Lee E Sanderson
(74) *Attorney, Agent, or Firm* — Studebaker & Brackett PC

(57) ABSTRACT

A laminate structure includes a first layer as a substrate and a second layer provided on the first layer. The second layer is composed of a rubber composition including a rubber component, first fine particles for providing a surface with irregularity, and second fine particles for shielding UV-C light. When performing Raman mapping analysis on a first peak derived from oscillation of the second fine particles in Raman scattering spectrum obtained by Raman scattering measurement of the second layer, the second layer includes a region where an intensity of the first peak is greater in an area where the first fine particles are not present than an area where the first fine particles are present.

19 Claims, 22 Drawing Sheets

(51) Int. Cl.
  *C09D 7/61* (2018.01)
  *C09D 183/00* (2006.01)
(58) Field of Classification Search
  CPC ............ B32B 2255/03; B32B 2255/04; B32B 2255/10; B32B 2255/40; C09D 183/04; C09D 183/06; C09D 183/08; C08K 2003/224; C08K 2003/2241; C08K 3/36; C08J 2383/04
  USPC .............................. 428/363.91, 36.92, 36.91
  See application file for complete search history.

(56) References Cited

U.S. PATENT DOCUMENTS

| | | | |
|---|---|---|---|
| 5,171,787 A * | 12/1992 | Zama | C08L 83/04 525/100 |
| 5,256,480 A * | 10/1993 | Inoue | B32B 25/042 428/408 |
| 5,346,760 A | 9/1994 | Lemoine et al. | |
| 10,465,270 B1 * | 11/2019 | Zhang | H01B 13/0036 |
| 11,041,091 B2 | 6/2021 | Kashimura et al. | |
| 2002/0019479 A1 * | 2/2002 | Ota | G03G 15/2057 524/588 |
| 2005/0074386 A1 * | 4/2005 | Valero | C01B 33/193 423/338 |
| 2009/0301750 A1 * | 12/2009 | George | H01B 7/295 524/413 |
| 2016/0252854 A1 * | 9/2016 | Oshima | G03G 15/2057 399/333 |
| 2021/0079258 A1 | 3/2021 | Kashimura et al. | |
| 2021/0079260 A1 | 3/2021 | Kashimura et al. | |
| 2021/0207000 A1 | 7/2021 | Kashimura et al. | |
| 2021/0238446 A1 | 8/2021 | Kashimura et al. | |
| 2022/0204769 A1 * | 6/2022 | Hasegawa | C08G 77/24 |

FOREIGN PATENT DOCUMENTS

| | | |
|---|---|---|
| JP | 2018-073830 A | 5/2018 |
| JP | 6723489 B1 | 6/2020 |

OTHER PUBLICATIONS

Extended European Search Report issued in the corresponding EP Application No. 23155000.5 dated May 15, 2023.
Communication pursuant to Article 94(3) EPC issued in EP 23 155 000.5 by the European Patent Office on May 7, 2024.

* cited by examiner

TiO₂ FINE PARTICLE

SILICONE RESIN PARTICLE

REGION A    REGION B

TiO₂ FINE PARTICLE

SILICONE RESIN PARTICLE

FIG. 17

LAMINATE STRUCTURE, CABLE AND TUBE

CROSS-REFERENCE TO RELATED APPLICATIONS

The present patent application claims the priority of Japanese patent application No. 2021-019099 filed on Feb. 9, 2021 and the priority of Japanese patent application No. 2021-098350 filed on Jun. 11, 2021, and the entire contents thereof are hereby incorporated by reference.

TECHNICAL FIELD

The present invention relates to a laminate structure, a cable and a tube.

BACKGROUND ART

Conventionally, a cable for medical devices made of silicone rubber including fine particles and with a layer that covers a sheath has been known (see Patent Literature 1). Compared with polyvinyl chloride (PVC), which has been commonly used as a material for sheath, silicone rubber has advantages such as little discoloration over time, but it tends to have low surface slidability.

Since the layer of the cable described in Patent Literature 1 is made of silicone rubber including fine particles, the surface of the cable is formed with irregularities (i.e., unevenness, indentations) derived from fine particles. This uneven surface makes it possible to reduce a contact area when the layer is in contact with other parts, thereby increasing the slidability of the surface of the layer, i.e., the slidability of the cable.

CITATION LIST

Patent Literature

Patent Literature 1: JP6723489B

SUMMARY OF THE INVENTION

Recently, as a method of sterilizing medical device cables, a sterilization method by UV-C light, by which the sterilization is easy, inexpensive, and reliable, is attracting attention. However, the resistance of the cable to the UV-C light is a problem in order to perform the sterilization by UV-C light. It has been confirmed that a cable equipped with a sheath made of silicone rubber will deteriorate when the UV-C light is repeatedly irradiated to the cable. Thus, the cable will have cracks in the sheath when stress such as bending the cable is applied to the sheath.

Therefore, the object of the present invention is to provide a laminate structure with silicone rubber as a base material, which is superior in resistance to UV-C light, and a cable and a tube with an insulator made of the laminate structure.

So as to achieve the above object, one aspect of the present invention provides: a laminate structure comprising:
  a first layer as a substrate; and
  a second layer being provided on the first layer and comprising a rubber composition including a rubber component, first fine particles for providing a surface with irregularity, and second fine particles for shielding UV-C light,
  wherein when performing Raman mapping analysis on a first peak derived from oscillation of the second fine particles in Raman scattering spectrum obtained by Raman scattering measurement of the second layer, the second layer includes a region where an intensity of the first peak is greater in an area where the first fine particles are not present than an area where the first fine particles are present.

Further, another aspect of the present invention provides: a cable or tube comprising an insulator comprising the above laminate structure.

Effect of the Invention

According to the present invention, it is possible to provide a laminate structure with silicone rubber as a base material, which is superior in resistance to UV-C light, and a cable and a tube with an insulator made of the laminate structure.

BRIEF DESCRIPTION OF DRAWINGS

FIG. 17 is a table showing representative observation images of surfaces of the sheath pieces cut from samples C1 to C11 after the bending test.

BEST MODE FOR CARRYING OUT THE INVENTION

The First Embodiment (Configuration of a Laminate Structure)

Figure 1:
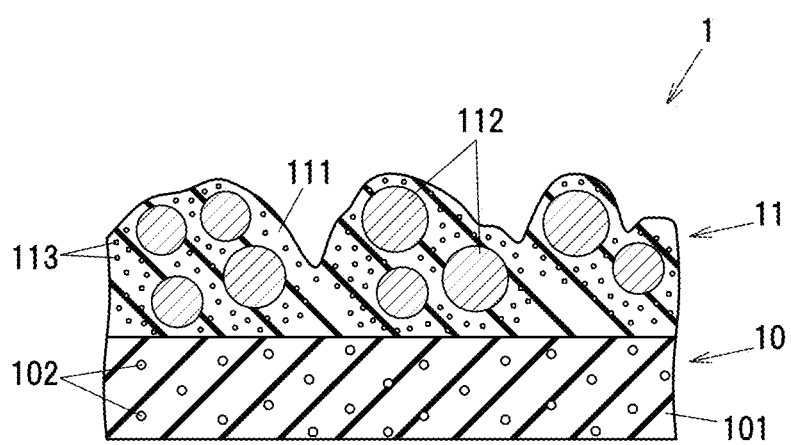
FIG. 1 is a vertical cross-sectional view of a laminate structure according to the first embodiment of the present invention.

FIG. 1 is a vertical cross-sectional view of a laminate structure 1 according to the first embodiment of the present invention. The laminate structure t is composed of a first layer 10 including silicone rubber as a base material (i.e., parent material), and a second layer 11 layered on the first layer 10. The second layer 11 includes silicone rubber as a base material 111, first fine particles 112 to give irregularities to a surface, and second fine particles 113 to shield UV-C light by absorption and/or scattering.

The first fine particles 112 are made of a material including Si such as silicone resin and silica that are more resistant to UV-C light than silicone rubber. It is also preferable that an average particle size of the second fine particles 113 is smaller than an average particle size of the first fine particles 112. For example, the average particle size of the second fine particles 113 is preferably ½ or less of the average particle size of the first fine particles 112, and more preferably ⅕ or less of the average particle size of the first fine particles 112. This allows the second fine particles 113 to be polarized around the first fine particle 112 and the second fine particles 113 to be selectively placed in areas where the first fine particles 112 are not present in an in-plane direction of the second layer 11. Here, UV-C light is an ultraviolet light within a wavelength range of 200 to 280 nm.

Silicone rubber, which is the base material for the first layer 10 and the second layer 11, is a kind of silicone resins. The silicone rubber is more resistant to ultraviolet light (e.g., UV-A light, UV-B light) than polyvinyl chloride, which is commonly used as a material for cables and tubes to be used in medical applications.

Silicone rubber also adds the first fine particle, 112, which contains Si, such as silicone resin particles (i.e., fine particles) and silica (silicon oxide) particles (i.e., fine particles), to create a surface that is uneven and irregular, thereby reducing the level of surface stickiness (i.e., tacking), and improving slidability (i.e., sliding properties). Therefore, the second layer 11 including the silicone rubber doped with the first fine particles 112 can be layered on the first layer 10 including the silicone rubber but free of the first fine particles 112 to cover the surface of the first layer 10, thereby reducing the surface stickiness of the silicone rubber and improving the slidability.

On the other hand, a silicone rubber that does not include the first fine particles 112 should have a certain thickness to have a performance as a base material (e.g., the function to protect or accommodate other articles) compared to a silicone rubber that includes the first fine particles 112. For this reason, it is preferable to use the laminate structure 1 as an insulator for cables and tubes, and to form the first layer 10 by extrusion or the like with high productivity, and then laminate the second layer 11 on the first layer 10 by coating or the like.

The laminate structure 1 may have various forms depending on its application. For example, when used as an insulator for cables and tubes, it is molded in a tubular form, and when used as high UV-resistant sheets for constant temperature greenhouse or UV-shield sheets (UV-shield curtains) to shield against UV leakage from sterilization rooms or the like.

(Configuration of the Second Layer)

The second layer 11 includes the first fine particles 112, which create the irregularities on the surface. This results in a smaller contact area and higher slidability, when the second layer 11 comes into contact with a contactant, as compared to a flat surface.

For the silicone rubber which is the base material 111 of the second layer 11, e.g., an addition reaction type silicone rubber coating agent or a condensation reaction type silicone rubber coating agent can be used. In particular, it is preferable to use the addition reaction type silicone rubber coating agent in order to ensure adhesion and wear resistance to the first layer 10 including the silicone rubber as the base material.

It is preferable that a thickness of the second layer 11 is not less than 3 μm to obtain good slidability and predetermined wipes resistance (i.e., resistance to being wiped off) of the surface of the laminate structure 1 by the second layer 11. Also, the second layer 11 may be laminated on both sides of the first layer 10. Although the upper limit of the thickness of the second layer 11 is not particularly limited, it is preferable to be not more than 100 μm from the viewpoint of productivity, high flexibility and high bending property.

The first fine particle 112 is, for example, a silicone resin fine particle, a silica particle, or a mixture of these two kinds of particles. The first fine particle 112, preferably has a higher hardness than the base material 111 composed of silicone rubber (e.g., the first fine particle 112 has a Shore (durometer A) hardness of not lower than 1.1 times the hardness of the base material 111).

Silicone resin with fewer reaction groups (e.g., methyl groups) than silicone rubber has a higher hardness than silicone rubber, and silica with no reaction group is more hardness. In terms of mass, silica is the largest, silicone resin is the second largest, and silicone rubber is the smallest.

From the viewpoint of reducing the deformation of the surface when the second layer 11 comes into contact with the contactant, silica with high hardness is the most preferable material for the first fine particles 112, and silicone resin is the next preferable material. This is because when a contact causes pressure on the surface of the second layer 11, the harder the first fine particle 112 can reduce the deformation of the surface of the second layer 11. This will reduce the increase in contact area between the second layer 11 and the contactant and maintain the slidability.

On the other hand, because of the large mass of silica as described above, the first fine particle 112 composed of silica is easily precipitated in the silicone rubber coating agent as a base material in the manufacturing process of the second layer 11. It is difficult to disperse the first fine particles 112 in silicone rubber (the second layer 11) compared to the first fine particles 112 composed of the silicone resin. Therefore, from the viewpoint of improving the uniformity of dispersion in silicone rubber (the second layer 11), it is preferable to use the first fine particles 112 composed of silicone resin.

Therefore, it is preferable to use the first fine particle 112 composed of silicone resin, to maintain the slidability when the second layer 11 comes into contact with the contactant and to achieve the uniformity of the dispersion of the first fine particles 112 in silicone rubber as the base material.

The average particle size of the first fine particles 112 is e.g., 1 μm or more and 10 μm or less. In addition, the concentration (mass %) of the first fine particles 112 in the second layer 11 is e.g., 10 mass % or more and 60 mass % or less. Here, the "average particle size" in the present application is measured by the laser diffraction scattering method.

As mentioned above, the first fine particle 112 is more resistant to UV-C light than the silicone rubber as the base material 111. This is because the bond energy between atoms in the molecular structure of silicone resin or silica, which is the material of the first fine particle 112, is higher than the bond energy between atoms in the molecular structure of silicone rubber.

For example, the binding energy of C—H bond, which is often contained in silicone rubber, is smaller (approximately 4.27 eV) than the energy of UV-C light (approximately 6.2 eV), so that the C—H bond is cut by UV-C light irradiation. Meanwhile, the binding energy of Si—O bond, which is often contained in the silicone resin, is greater (approximately 6.52 eV) than the energy of UV-C light, so that the Si—O bond does not break due to exposure of UV-C light.

The second fine particle 113 is composed of a material, which has the characteristics of shielding UV-C light by absorbing and/or scattering it, such as titanium oxide ($TiO_2$), carbon (C), zinc oxide (ZnO), and iron oxide ($Fe_2O_3$). Since the second fine particles 113 shield UV-C light, it is possible to reduce the degradation caused by UV-C light in the base material 111, which is composed of silicone rubber. Titanium oxide as a material of the second fine particle 113 can be either anatase, rutile, or brookite, and can be a mixture of two or more of them. In addition, titanium oxide may be supplemented with niobium oxide to provide stability.

As noted above, it is preferable that the average particle size of the second fine particles 113 is smaller than the average particle size of the first fine particles 112. By reducing the average particle size of the second fine particles 113, the second fine particle 113 can be present in a gap space between the first fine particles 112. By reducing the average particle size of the second fine particles 113 to be smaller than the average particle size of the first fine particles 112, the second fine particles 113 can be polarized around the first fine particle 112, and the second fine particles 113 can be selectively placed in regions where the first fine particle 112 is not present along the in-plane direction of the second layer 11. For example, if the average particle size of the second fine particles 113 is ½ or less, and more preferably ⅕ or less, of the average particle size of the first fine particles 112, the second fine particles 113 can be more effectively polarized around the first fine particle 112. The lower limit of the average particle size of the second fine particles 113 is not particularly limited, but from the viewpoint of availability, it is preferable that the average particle size of the second fine particles 113 is 10 nm or more. Here, the "average particle size" of the second fine particles 113 was measured by laser diffraction scattering method.

The region in which the first fine particle 112 is not present when the second layer 11 is observed from the surface (the area located between the first fine particles 112) is a region that is less resistant to UV-C light, where only the base material 111 composed of silicone rubber is present. The inventors of the present application found that it is possible to effectively improve resistance to UV-C light by selectively placing the second fine particles 113 in this region and thereby shielding UV-C light.

(The First Layer Configuration)

The first layer 10 preferably includes a second fine particle 102 to absorb UV-C light, as well as the second layer 11 including the second fine particle 113, so as reduce degradation caused by UV-C light transmitted through the second layer 11. In this case, the first layer 10 includes a base material 101 composed of silicone rubber and the second fine particles 102 distributed in the base material 101, as shown in FIG. 1. For a material of the base material 101, polyethylene, chlorinated polyethylene, chloroprene rubber, polyvinyl chloride (PVC), polyurethanes and the like can be used. Among them, silicone rubber and chloroprene rubber are preferable from a viewpoint of chemical resistance and heat resistance. If the first layer 10 is used as the sheath material, the first layer 10 may be composed of an insulating material with the addition of common formulations such as various crosslinkers, crosslinking catalysts, anti-aging agents, plasticizers, lubricants, fillers, flame retardants, stabilizers, colorants, and the like. It is also possible to mix organic ultraviolet absorbers instead of the second fine particles 102, which is dispersed in the base material 101.

The material of the second fine particle 102 may be the same as the material of the second fine particle 113, e.g., titanium oxide, carbon. However, it is preferable that the second fine particles 102 are evenly distributed in the base material 101 so that the resistance to UV-C light in the first layer 10 does not vary depending on the location. For this reason, the average particle size of the second fine particles 102 is not particularly limited, but it is preferable to be, e.g., 10 nm or more and 1 μm or less. Here, the "average particle size" of the second fine particles 102 was measured by laser diffraction scattering method.

($TiO_2$ Fine Particle)

Figure 2:
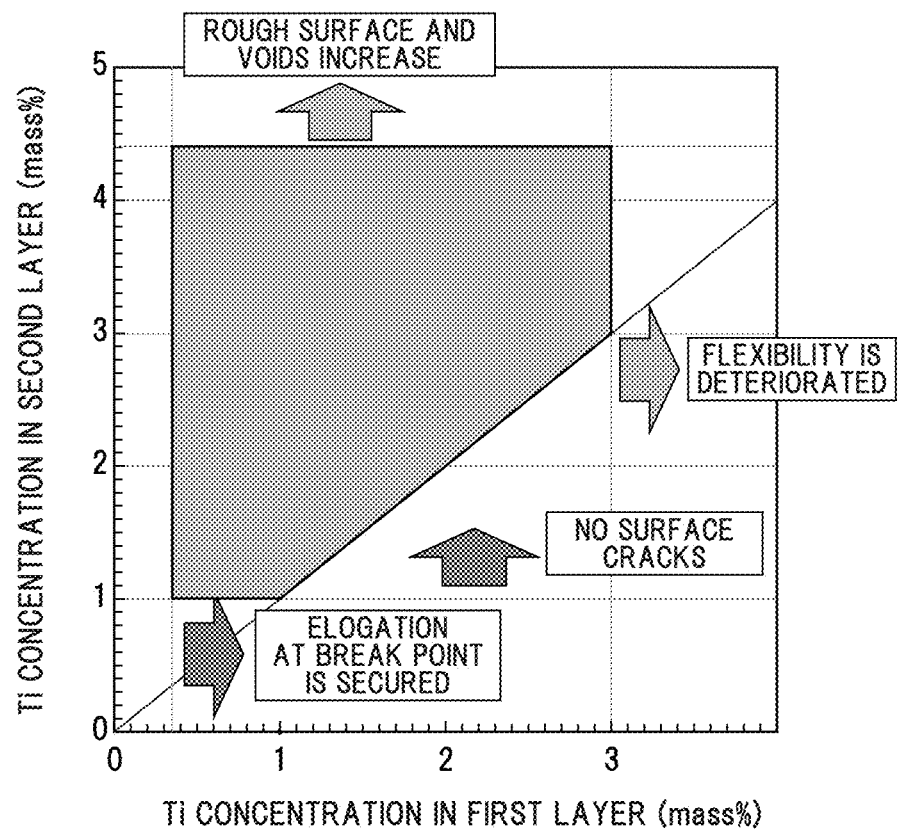
FIG. 2 is a graph showing preferred ranges of Ti concentration in a first layer and Ti concentration in a second layer.

FIG. 2 is a graph showing preferred ranges of Ti concentration in the first layer 10 including $TiO_2$ fine particles 102 as the second fine particles and Ti concentration in the second layer 11 including $TiO_2$ fine particles 113 as the second fine particles.

As shown in FIG. 2, the Ti concentration in the first layer 10 is preferably 0.35 mass % or more and 3.0 mass % or less. By including $TiO_2$ fine particles 102 at a Ti concentration of 0.35 mass % or more in the first layer 10, it is possible to maintain the high elongation at break measured when the tensile test specified in "JIS K6251 (1994)" is performed after UV-C light is irradiated on the cable including the laminate structure 1 as insulators (sheath and its layer).

Figure 8A:
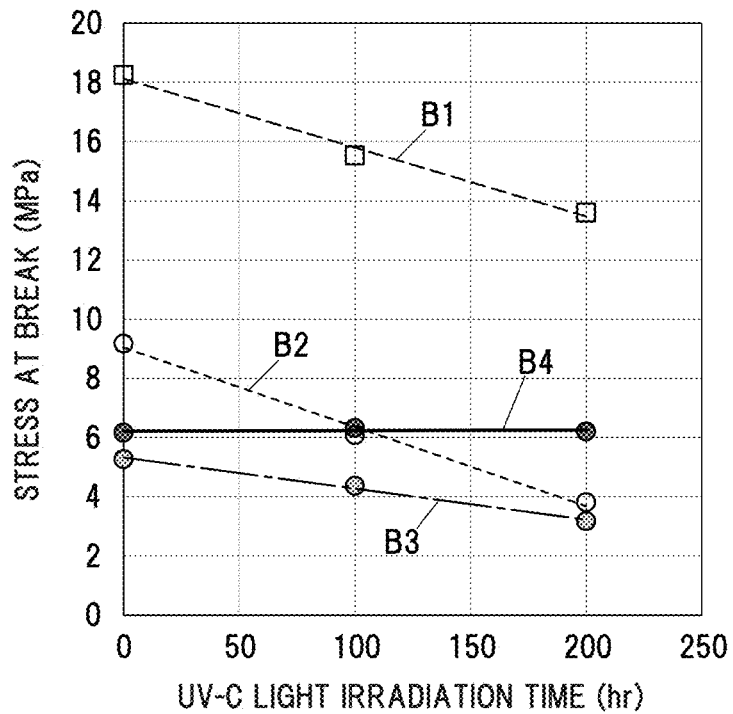
FIG. 8A is a graph showing the relationship between the irradiation time of UV-C light and the stress at base break for samples B1 to B4.
Figure 8B:
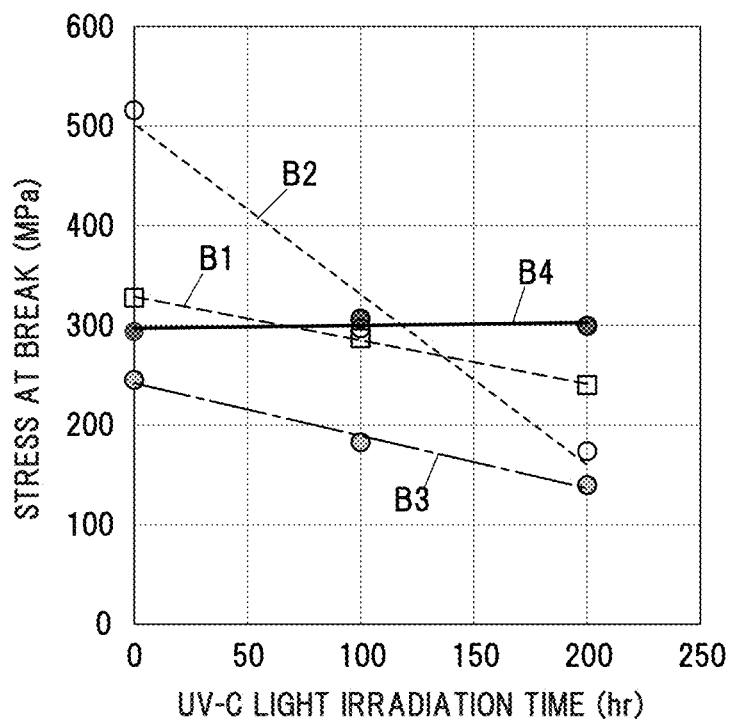
FIG. 8B is a graph showing the relationship between the irradiation time of UV-C light and the elongation of the base during the break for samples B1 to B4.

The goal was set to achieve an elongation at break of 250% or more after exposure of UV-C light of 1404 J/cm$^2$ since the elongation at break is at least 250% when the UV-C light was not irradiated to the laminate structure 1 with the second layer 11 that does not include the TiO$_2$ fine particles 102 (See FIG. 8B).

The goal was set to achieve an elongation at break of 150% or more even after exposure to UV-C light of 2808 J/cm$^2$, since the elongation at break required for general rubber materials is at least 150%.

The specific method of this tensile test will be described below.

On the other hand, when the first layer 10 includes TiO$_2$ fine particles 102 at a Ti concentration greater than 3.0 mass %, the first layer 10 will be stiffened, resulting in lower flexibility of the laminate structure 1 and lower tearing strength. Therefore, considering the handling of cables and tubes when the first layer 10 is used as the insulator for cables and tubes, the Ti concentration in the first layer 10 is preferably not greater than 3.0 mass %.

As shown in FIG. 2, the Ti concentration in the second layer 11 is preferably 1.0 mass % or more and 4.4 mass % or less. By including TiO$_2$ fine particles 113 at a Ti concentration of 1.0 mass % or more in the second layer 11, it is possible to suppress the formation of cracks, which may reach of the first layer 10, on the surface of the laminate structure 1, due to bending test equivalent to 45% to 50% tensile after exposure to UV-C light at 1404 J/cm$^2$. The method of the bending test and observation of the presence of cracks will be described below.

On the other hand, when the second layer 11 includes TiO$_2$ fine particles 113 at a Ti concentration greater than 4.4 mass %, the surface roughness of the second layer 11 will be greater. As the surface roughness increases, dirt and bacteria are easily attached and difficult to be removed. In the case where the second layer 11 includes the first fine particle 112, such as silicone resin fine particles, when the second layer 11 includes TiO$_2$ fine particles 113 at a Ti concentration greater than 4.4 mass %, the adhesion between the base material 111 composed of silicone rubber and the first fine particle 112 is reduced, making it easier for the first fine particle 112 to fall off, and the sliding property of the surface of the second layer 11 is reduced. Therefore, the Ti concentration in the second layer 11 is preferably not greater than 4.4 mass %.

Also, as shown in FIG. 2, the concentration of TiO$_2$ fine particle 113 in the second layer 11 is preferably higher than the concentration of TiO$_2$ fine particle 102 in the first layer 10, i.e., the Ti concentration of the second layer 11 is preferably higher than the Ti concentration of the first layer 10. By setting the concentration of TiO$_2$ fine particle 113 in the second layer 11 to be higher than the concentration of TiO$_2$ fine particle 102 in the first layer 10, it is possible to effectively absorb and/or scatter UV-C light in the second layer 11, thereby suppressing degradation caused by UV-C light in the first layer 10, and thus suppressing the reduction in flexibility and tearing strength of the laminate structure 1.

All Ti in the first layer 10 are contained in TiO$_2$ fine particles 102, and all Ti in the second layer 11 are contained in TiO$_2$ fine particles 113. The Ti concentration in the first layer 10 and the Ti concentration in the second layer 11 are determined as the mean values in a measuring area of 125 μm wide×95 μm high using an energy dispersive X-ray analyzer (EDS) mounted on a scanning electron microscope (SEM).

The Second Embodiment

The second embodiment of the present invention is a cable or tube with an insulator composed of the laminate structure 1 in the first embodiment. Next, the cable to be used as a medical ultrasonic probe cable is described below.

In recent years, it has been considered that silicone rubber, which has superior heat resistance and chemical resistance, is used as the material for sheath in cables used for medical applications. However, as mentioned above, silicone rubber has a problem of poor slidability. Therefore, when silicone rubber is used as the material for the sheath of the cable, the problems that the cable can easily be caught with other parts and that dust can easily get on the surface of the cable will occur.

In particular, if the cable is more easily caught with other parts, it will be difficult to handle the cable connected to medical devices such as ultrasonic imaging devices. This is because the examination is performed while moving the ultrasonic probe connected to the probe cable around the human body. If the probe cable is easily caught with other cables or clothing, it will not be possible to move the ultrasonic probe smoothly. Therefore, it is desired that cables used for medical applications have no stickiness and good surface slidability (static friction coefficient of 0.5 or less).

Figure 3:
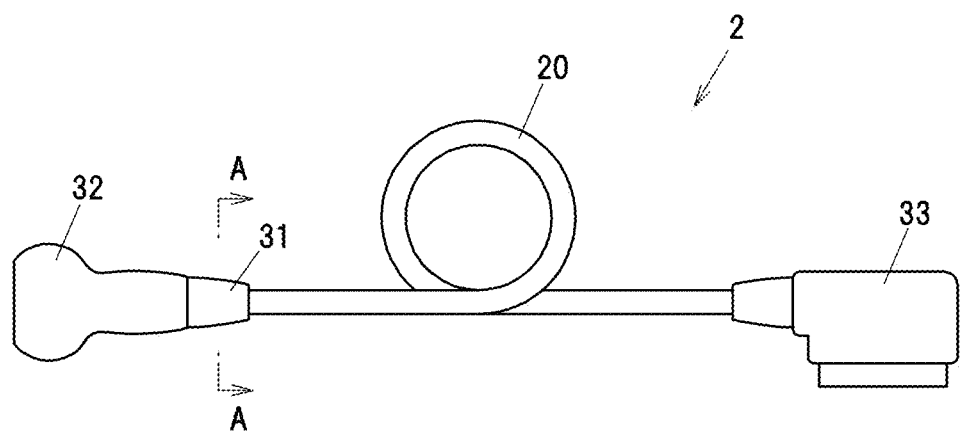
FIG. 3 is a schematic diagram of a configuration of an ultrasonic probe cable according to the second embodiment of the present invention.

FIG. 3 shows a schematic diagram of the configuration of an ultrasonic probe cable 2 in the second embodiment of the present invention. In the ultrasonic probe cable 2, an ultrasonic probe 32 is attached to one end of a cable 20 via a boot 31, which protects the one end, as shown in FIG. 3. Meanwhile, a connector 33 that connects to a main body of an ultrasonic imaging device is attached to the other end of the cable 20.

Figure 4A:
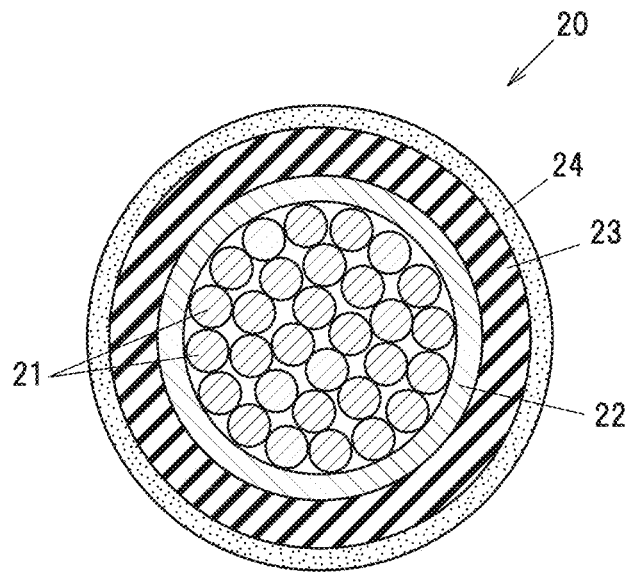
FIG. 4A is a radial cross-sectional view of the ultrasonic probe cable.

FIG. 4A shows a radial cross-sectional view of the cable 20 of the ultrasonic probe cable 2. The cable 20 includes, for example, plural electric wires 21, typically coaxial cables, and a shield 22, such as a braided shield, to cover the plural electric wires 21. And a sheath 23 is provided to cover the shield 22. In addition, the cable 20 includes a coating film (i.e., layer) 24 covering a circumference of the sheath 23 and adhering to the sheath 23.

Figure 4B:
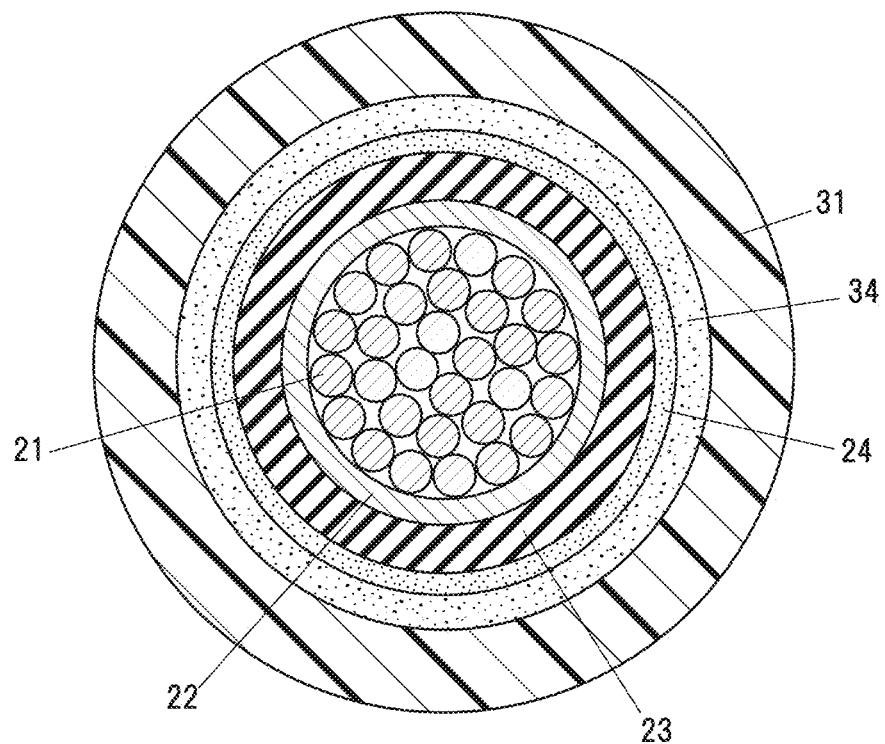
FIG. 4B is a radial cross-sectional view of the ultrasonic probe cable cut along A-A line in FIG. 3.

FIG. 4B shows a radial cross-sectional view of the ultrasonic probe cable 2 cut along a line A-A in FIG. 3. The boot 31 is installed over the coating film 24 over an adhesive layer 34 covering the coating film 24 as shown in FIG. 4B. The adhesive layer 34 is formed from, e.g., silicone adhesive or epoxy adhesive. Also, the boot 31 may be formed from, e.g., PVC, silicone rubber, chloroprene rubber, etc., and the boot 31 preferably includes the second fine particles 102 or organic UV absorbers to shield UV-C light, similarly to the first layer 10.

The sheath 23 and the coating film 24 of the cable 20 are respectively composed of the first layer 10 and the second layer 11 of the laminate structure 1. In other words, in the cable 20, the laminate structure 1 is used as the sheath 23 and the coating film 24. By using the coating film 24 composed of the second layer 11, which is superior in sliding property, it is possible to suppress the ultrasonic probe cable 2 from being caught due the stickiness of the surface of the sheath 23. For example, the thickness of the coating film 24 is 3 μm or more and 100 μm or less. The illustration of the second fine particles 102 in the sheath 23 and the first fine particles 112 and the second fine particles 113 in the coating film 24 are omitted.

The following is an example of a method for manufacturing the ultrasonic probe cable 2 in the present embodiment. First, plural (e.g., 100 or more) of electric wires 31 are bundled together. The shield 22 is then formed to cover the bundle of the electric wires 21.

Then, to cover the shield 22, the first layer 10 and the second layer 11 of the laminate structure 1 are formed in this order, then the sheath 23 and the coating film 24 are formed. The sheath 23 is formed by extrusion molding using e.g., an extruder. The coating film 24 is formed by, e.g., dipping, spraying or rolling application method. In the dipping method, the ultrasonic probe cable 2 formed up to the sheath 23 is pulled up through a liquid coating material to form the coating film 24 on a surface of the sheath 23. This dipping method is superior to the spraying or rolling application methods in terms of uniformity of a film thickness of the coating film 24 to be formed.

The liquid coating agent used in the dipping method is a liquid silicone rubber including the first fine particles 112 and the second fine particles 113 and contains a solvent such as n-heptane. By adjusting the content of the first fine particles 112 and the second fine particles 113 in this liquid coating agent, the content of the first fine particles 112 and the second fine particles 113 in the coating film 24 can be controlled.

Next, the configuration of a tube (hollow tube) to be used for medical applications such as catheters will be described below, as another example of cables or tubes with insulators composed of the laminate structure 1.

Figure 5A:
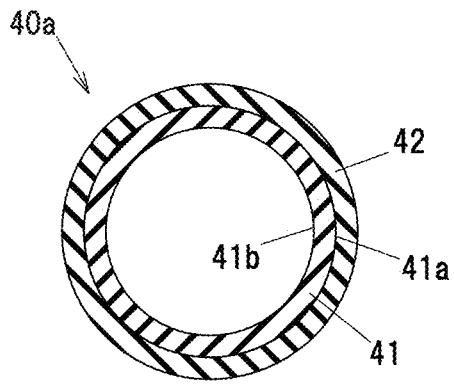
FIGS. 5A to 5C are radial cross-sectional view of medical tubes according to the second embodiment of the present invention.
Figure 5B:
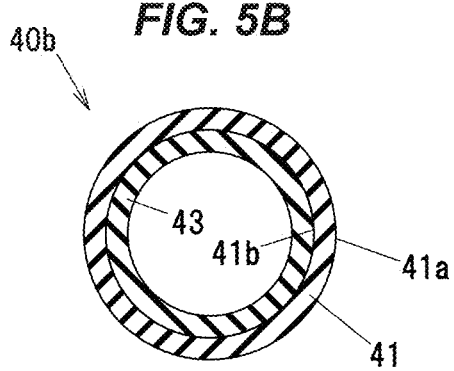
Figure 5C:
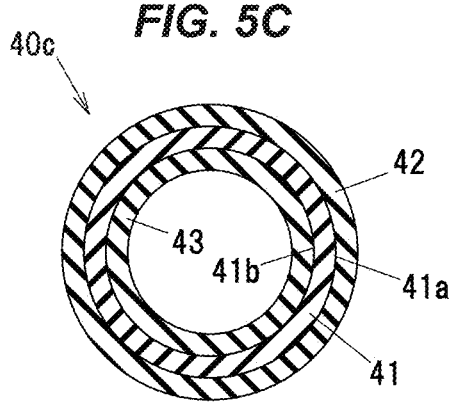

FIGS. 5A to 5C are cross-sectional views of a medical tube in the second embodiment of the present invention. A medical tube 40a shown in FIG. 5A has an outer layer 42 on an outer surface 41a of a tube main body 41. A medical tube 40b shown in FIG. 5B has an inner layer 43 on an inner surface 41b of the tube main body 41. A medical tube 40c shown in FIG. 5C has an outer layer 42 and an inner layer 43 respectively on an outer surface 41a and an inner surface 41b of the tube main body 41.

As shown in examples of the medical tubes 40a, 40b, and 40c, the tube in the present embodiment includes the tube main body 41, and the outer layer 42 covering the outer surface 41a of the tube main body 41 or the inner layer 43 covering the inner surface 41b of the tube main body 41, or alternatively, both the outer layer 42 and the inner layer 43. The tube main body 41 of the medical tubes 40a, 40b, and 40c is composed of the first layer 10 of the laminate structure 1, and the outer layer 42 and the inner layer 43 are respectively composed of the second layer 11 of the laminate structure 1.

Because the tubes in the present embodiment have excellent slidability at the inner surface or the outer surface, for example, when devices are inserted into the tubes, such as catheters or other medical tubes, smooth insertion and removal of the devices can be achieved. Further, the tubes in the present invention may be used as tube sets for endoscopic surgical instruments, tube sets for ultrasonic surgical instruments, blood analyzer tubes, tubes within oxygen concentrators, artificial dialysis blood circuits, artificial cardiopulmonary circuits (artificial heart-lung circuits), endotracheal tubes, and so on.

Effect of the Embodiments

According to the laminate structure 1 in the first embodiment, the surface has excellent slidability because the second layer 11 includes the first fine particles 112, and the second fine particles 113 are polarized around the first fine particle 112, which makes the laminate structure 1 more resistant to UV-C light. In addition, according to the ultrasonic probe cable 2 and the medical tubes 40a, 40b, 40c, etc., in the second embodiment, because the laminate structure 1 is used as an insulator, the ultrasonic probe cable 2 and the medical tubes 40a, 40b, 40c, etc., have excellent surface slidability and are resistant to UV-C light.

In the first embodiment, silicone rubber is used as the material for the base material 111 in the second layer 11 of the laminate structure 1. However, the same effect can be achieved by using rubber components other than silicone rubber, such as chloroprene rubber, instead of silicone rubber.

Example 1

(Preparation of the Laminate Structure 1)

Four samples (samples A1 to A4) were prepared to verify the shielding effect of UV-C light in the second layer 11 of the laminate structure 1. First, a cable core was prepared by stranding two-hundreds coaxial cables each with a diameter of about 0.25 mm and covering the stranded cables with a braided wire. Then, by using an extruder, a sheath material was extruded at a speed of 5 m/min to cover an outer periphery of the cable core, and the sheath 23 with a thickness of 0.8 mm was formed as the first layer 10 of the laminate structure 1 (an outer diameter of the cable was about 8 mm). Here, for the sheath material of the sample A1, a commonly used PVC was used. For the sheath material of the samples A2 to A4, a color batch including titanium oxide (a mixture of "KE-color-W" and "KE-174-U" made by Shin-Etsu Chemical Co., Ltd.) was used. The mixture was adjusted in such a manner that Ti concentration analyzed by an energy dispersive X-ray analyzer (EDS) mounted on a scanning electron microscope (SEM) (average value in the measuring area of 125 μm wide×95 μm high) is 0.12 mass %. By the process so far, the samples A1 and A2, which do not have a coating film 24 as the second layer 11 of the laminate structure 1, were prepared.

Next, a material for forming the coating film 24 of the sample A3 was prepared. An addition reaction type silicone rubber coating agent (product name: SILMARK-TM, made by Shin-Etsu Chemical Co., Ltd.) was prepared as a rubber component as the base material 111. As the first fine particles 112, silicone resin fine particles with an average particle size of 5 μm (product name: X-52-1621, made by Shin-Etsu Chemical Co., Ltd.) were prepared. For 100 parts by mass of this rubber component, 120 parts by mass of silicone resin fine particles, 600 parts by mass of toluene as a solvent for viscosity adjustment, and 8 parts by mass of crosslinking agent (product name: CAT-TM, made by Shin-Etsu Chemical Co., Ltd.), and 0.3 parts by mass of curing catalyst (product name: CAT-PL-2, made by Shin-Etsu Chemical Co., Ltd.) were mixed, to prepare a coating solution with a ratio of 55 mass % of the first fine particles 112 to the coating film 24. The content of the first fine particles 112 in the coating film 24 was calculated assuming that the coating agent cures with little or no mass reduction (approximately equivalent to the compound mass ratio).

Then, the surface of the sheath 23 provided on the cable core was cleaned. The sheath 23 was then immersed in the above coating solution using the dip coating method, and a coating composed of silicone rubber was formed on the sheath surface. After that, the coating was thoroughly dried and cured at a temperature of 150° C. to form the coating film 24 with uneven surface. The thickness of the coating film 24 of the sample A3 thus obtained was 15 μm. The sample A3 was prepared by the above process.

Next, the material for forming the coating film 24 of the A4 sample was prepared. For the coating film 24 of the A4 sample, the rubber component as the base material 111 and the silicone resin fine particles as the first fine particles 112 were prepared similarly to the materials used for the coating film 24 of the A3 sample. In addition, as the second fine particle 113, titanium oxide (anatase-type $TiO_2$) fine particles with an average particle size of 250 nm were prepared. For 100 parts by mass of the rubber component, 120 parts by mass of silicone resin fine particles, titanium oxide fine particles, 600 parts by mass of toluene as a solvent for viscosity adjustment, and 8 parts by mass of crosslinking agent (product name: CAT-TM, made by Shin-Etsu Chemical Co., Ltd.), and 0.3 parts by mass of curing catalyst (product name: CAT-PL-2, made by Shin-Etsu Chemical Co., Ltd.) were mixed, to prepare a coating solution with a ratio of 55 mass % of the first fine particles 112 to the coating film 24 and a predetermined concentration of the second fine particles 113 to the coating film 24. The concentration of titanium oxide fine particles as the second fine particles 113 in the coating film 24 was adjusted in such a manner that Ti concentration in the coating film 24 analyzed by an energy dispersive X-ray analyzer (EDS) mounted on a scanning electron microscope (SEM) (mean value in the measuring area of 125 μm wide×95 μm high) is 0.6 mass %. The content of the first fine particles 112 in the coating film 24 was calculated assuming that the coating agent cures with little or no mass reduction (approximately equivalent to the compound mass ratio).

Then, as with the coating film 24 of the sample A3, the surface of sheath 23 was cleaned, the coating film was formed by the dip coating method, and the coating film was dried and cured. The coating film 24 was formed with uneven surface. The thickness of the coating film 24 of the sample A4 thus obtained was 15 μm. The sample A4 was prepared by the above process.

(Verification of UV-C Light Shielding Effect)

To verify the UV-C light shielding effect in the second layer 11 of the laminate structure 1, a tensile test was performed on the samples A1 to A4 before and after UV-C light exposure. First, the sheath 23 of each of the cable-like samples A1 to A4 (the sheath 23 covered with the coating film 24 in the samples A3 and A4) was cut along the length direction, the content in the sheath 23 was removed and the sheath 23 was opened. The opened sheath 23 was punched with dumbbell-shaped punch No. 6 to form a dumbbell test piece (thickness of 0.8 mm). Here, the dumbbell test pieces made from the sheaths 23 of the samples A1, A2, A3, and A4 (the sheath 23 covered with the coating film 24 in the samples A3 and A4) are samples B1, B2, B3, and B4, respectively. Table 1 below shows the compositions of the samples B1 to B4.

TABLE 1

| | Sheath | | Coating film | | |
|---|---|---|---|---|---|
| | Parent material | The second fine particle | Parent material | The first fine particle | The second fine particle |
| B1 | PVC | — | None | — | — |
| B2 | Silicone rubber | Anatase $TiO_2$ (Ti: 0.12 mass %) | None | — | — |
| B3 | Silicone rubber | Anatase $TiO_2$ (Ti: 0.12 mass %) | Silicone rubber | Average particle size: 5 μm Silicone resin | None |
| B4 | Silicone rubber | Anatase $TiO_2$ (Ti: 0.12 mass %) | Silicone rubber | Average particle size: 5 μm Silicone resin | Anatase $TiO_2$ (Ti: 0.6 mass %) |

The tensile test is a test specified in "JIS K6251 (1994)" and was performed on the above samples B1 to B4 under the condition at an ambient temperature of 15 to 35° C., an ambient humidity of 28 to 65% under an atmospheric pressure. UV-C light irradiation was performed by a storage chamber with sterilization lamps (Storage chamber DM-5, lamps GL-10, available from Daishin Kogyo Co., Ltd.) at a chamber temperature of 25 to 40° C., a chamber humidity of 28% to 65%, a chamber pressure of 1 atm (atmospheric pressure), a wavelength of 253.7 nm, an illuminance of 1.3 mW/cm$^2$, and irradiation times of 100 hours and 200 hours. The illuminance meter was UVC-254A made by MK Scientific Inc.

Figure 6A:
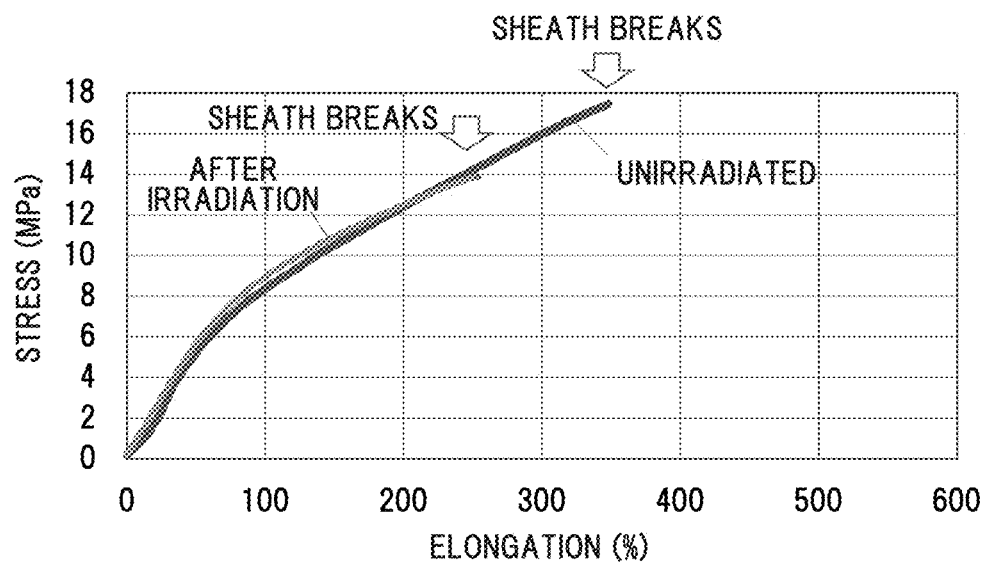
FIG. 6A is a graph showing the results of the tensile test of sample B1.

FIG. 6A shows the results of the tensile test of the sample B1. In FIG. 6A, "unexposed" shows the sample B1 before being exposed to UV-C light, and "after" shows the sample B1 after being exposed to UV-C light irradiation for 200 hours. As shown in FIG. 6A, it was confirmed that after exposure of UV-C light, the strength (magnitude of stress when the base member is broken) and the elongation are smaller than before exposure, and that the sample B1 deteriorates (changes to break easier) with the exposure of UV-C light. Moreover, because the sample B1 was a gray PVC, it was visually confirmed that the UV-C light irradiation caused a discoloration that would appear yellow. Here, 100% elongation indicates that the length of the Dumbbell test piece has doubled from the original length.

Figure 6B:
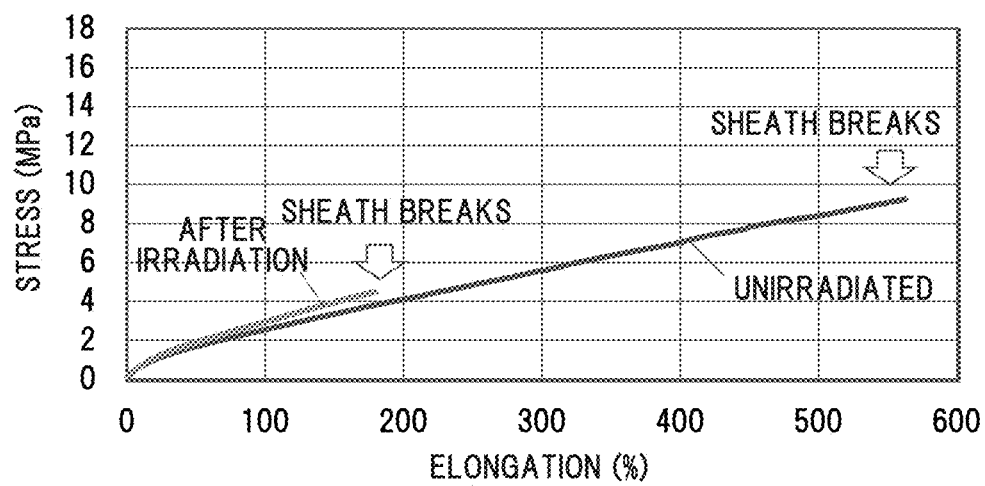
FIG. 6B is a graph showing the results of the tensile test of sample B2.

FIG. 6B shows the results of the tensile test of the sample B2. In FIG. 6B, "unexposed" shows the sample B2 before being exposed to UV-C light, and "after" shows the sample B2 after being exposed to UV-C light irradiation for 200 hours. As shown in FIG. 6B, it was confirmed that after exposure of UV-C light, the strength and the elongation are smaller than before exposure, and that the sample B2 deteriorates (alters) with the exposure of UV-C light. In addition, discoloration of the sample B2 (white) composed of silicone rubber due to exposure to UV-C light was not visually confirmed. On the other hand, compared with the graph in FIG. 6A, it is found that silicone rubber is more affected by UV-C light than PVC.

The sample B2 includes $TiO_2$ fine particles as the second fine particles that absorb UV-C light, but at a low level (Ti concentration in the sheath 23 is 0.12 mass %). It is therefore thought that the resistance to UV-C light had little effect. In addition, since the sample B2 does not have a coating film corresponding to the second layer 11, it is inferior in sliding property to the samples B3 and B4.

Figure 7A:
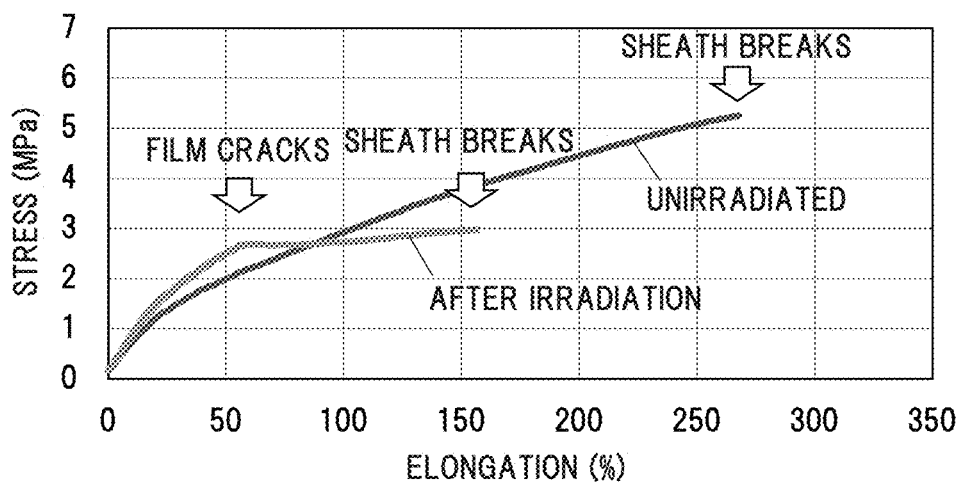
FIG. 7A is a graph showing the results of the tensile test of sample B3.

FIG. 7A shows the results of the tensile test of the sample B3. In FIG. 7A, "unexposed" shows the sample B3 before being exposed to UV-C light, and "after" shows the sample B3 after being exposed to UV-C light irradiation for 200 hours. As shown in FIG. 7A, it was confirmed that after exposure of UV-C light, the strength and the elongation are smaller than before exposure, and that the sample B3 deteriorates with the exposure of UV-C light. In addition, discoloration of the sample B3 (white) due to exposure to UV-C light was not visually confirmed similarly to the sample B2.

According to FIG. 7A, cracks have occurred in the coating film 24 corresponding to the second layer 11 around the elongation of more than 50%. The coating film 24 of the sample B3 includes silicone resin fine particles as the first fine particle 112, which are resistant to UV-C light. It is therefore thought that the silicone rubber in the region where the silicone resin fine particles are not present deteriorated so that the clacks occurred.

Figure 7B:
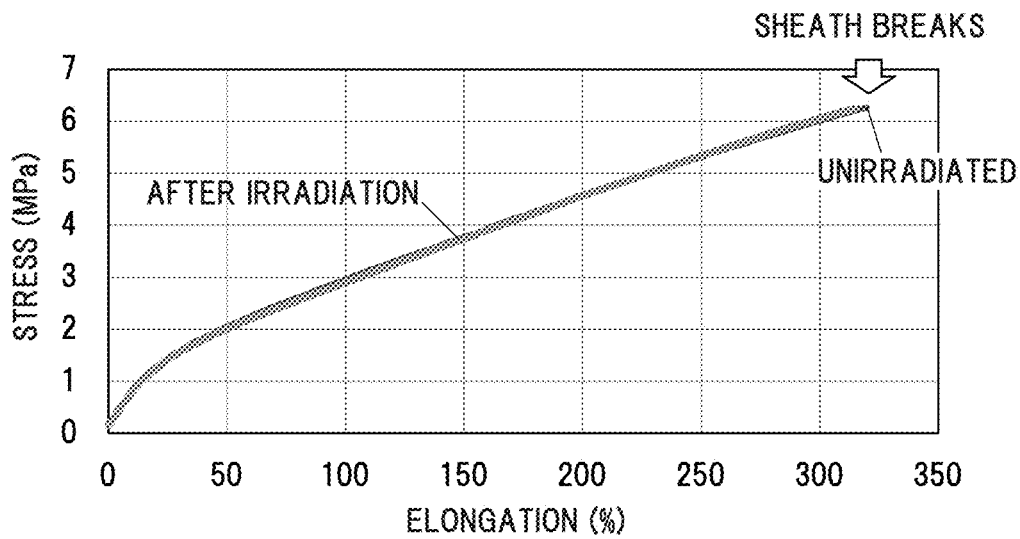
FIG. 7B is a graph showing the results of the tensile test of sample B4.

FIG. 7B shows the results of the tensile test of the sample B4. In FIG. 7B, "unexposed" shows the sample B4 before being exposed to UV-C light, and "after" shows the sample B4 after being exposed to UV-C light irradiation for 200 hours. As shown in FIG. 7B, it was confirmed that after exposure of UV-C light, the strength and the elongation are substantially the same before and after exposure, and that deterioration of the sample B4 due to the exposure of UV-C light was effectively suppressed. In addition, discoloration of the sample B4 (white) due to exposure to UV-C light was not visually confirmed similarly to the sample B2.

When comparing the test results of the sample B4 with the test results of the sample B3, it is found that titanium oxide fine particles, which are the second fine particles in the coating film corresponding to the second layer 11, have shielded UV-C light and suppressed the degradation.

FIG. 8A shows the relationship between the irradiation time of UV-C light and the stress at break of the substrate for the samples B1 to B4. FIG. 8B shows the relationship between the irradiation time of UV-C light and the elongation at break of the substrate for the samples B1 to B4.

According to FIGS. 8A and 8B, the sample B3, which does not include titanium oxide fine particles as second fine particles in the coating film corresponding to the second layer 11, has decreased in strength and elongation with increased irradiation time of UV-C light. On the other hand, the sample B4 including titanium oxide fine particles as the second fine particles in the coating film corresponding to the second layer 11 has no change in strength and elongation, even if the irradiation time of UV-C light increases. In addition, the sample B4 has a lower elongation before exposure of UV-C light than the sample B1, but the elongation after 200 hours of exposure of UV-C light is superior to the sample B1. These results also show that titanium oxide fine particles in the coating film of the sample B4 can suppress the progression of degradation caused by UV-C light.

Example 2

Raman mapping analysis was performed to determine the distribution of the second fine particles 113 in the second layer 11 of the laminate structure 1. In the Raman mapping analysis, Raman scattering measurements are performed while scanning the laser on the surface of the sample, and the information obtained from Raman scattering spectrum at each measurement point is mapped in two dimensions. The Raman mapping analysis was performed using the samples prior to UV-C light exposure.

Tables 2 and 3 below show the measurement and mapping conditions for the Raman scattering measurements, respectively. The Raman scattering measurements were performed using the RAMANforce Standard VIS-NIR-HS made by Nanophoton Corporation. The Raman scattering measurements were conducted at an ambient temperature of 15 to 35° C., an ambient humidity of 25 to 65% under atmospheric pressure.

TABLE 2

| Experiment | |
|---|---|
| Excitation wavelength | 532.06 nm |
| ND filter | 6.27% (200/255) |
| Central wavenumber of the spectrometer | 2450.00 cm$^{-1}$ |
| Diffraction grating | 300 gr/mm |
| Slit width | 50 μm |
| Exposure time | 1 s |
| Number of accrual counts | 1 |
| Objective lens | TU Plan Fluor 100x/NA 0.90 |
| Measurement mode | XY Mapping |
| Z track | ON |
| Measurement order | Vertical |
| Sample temperature | 24.5° C. (room temperature) |

TABLE 3

| Mapping criteria | |
|---|---|
| Width of the mapping area | 75 pixels |
| Height of the mapping area | 75 pixels |
| Total number of pixels | 5625 pixels |
| Spectral length | 1340 pixels |
| Data size | 7537500 pixels |
| Pixel aspect ratio | 1.000 |
| Horizontal pixel size | 300.0 nm |
| Vertical pixel size | 300.0 nm |
| Measuring range (width) | 22.5 μm |
| Measuring range (height) | 22.5 μm |

The mapping analysis for this example was performed on the surface of sheet-like silicone rubber layers (samples E1 to E4) as four types of the second layer 11. All samples E1 to E4 includes silicone rubber as the base material 111, silicone resin fine particles with an average particle size of approximately 2 μm as the first fine particles 112, titanium oxide fine particles, mainly including anatase-type $TiO_2$ fine particles with an average particle size of approximately 250 nm as the second fine particles 113. The content of the silicone resin fine particles in each of the samples E1 to E4 is 60 mass %. The content of silicone resin fine particles in each of the samples E1 to E4 was calculated based on the assumption that silicone rubber coating agent cures with little or no mass reduction (approximately equivalent to the compound mass ratio). Specifically, the mass of silicone resin fine particles is divided by the total mass of silicone resin fine particles, titanium oxide fine particles and silicone rubber.

Table 4 below shows the silicone resin fine particles as the first fine particles 112 and the silicone resin concentration in each sample, and the average particle size of titanium oxide fine particles as the second fine particles 113 and the Ti concentration in each sample, in the samples E1 to E4. The Ti concentration in Table 4 was determined by the SEM-EDS (the average value in the measuring area of 125 μm wide by 95 μm high). The sample E1 is equivalent to the sample A4 (B4).

TABLE 4

| | First fine particle | | Second fine particle | |
|---|---|---|---|---|
| | Average particle size (μm) | Silicone resin concentration (mass %) | Average particle size (nm) | Ti concentration (mass %) |
| E1 | 5 | 60 | 250 | 0.6 |
| E2 | 5 | 60 | 250 | 1.1 |
| E3 | 5 | 60 | 250 | 1.5 |
| E4 | 5 | 60 | 250 | 4.4 |

The samples E1 to E4 differ in the amount of titanium oxide fine particles as the second fine particles 113. The Ti concentrations (as measured by SEM-EDS) of the samples E1, E2, E3, and E4 are 0.6 mass %, 1.1 mass %, 1.5 mass %, and 4.4 mass %, respectively.

Figure 9:
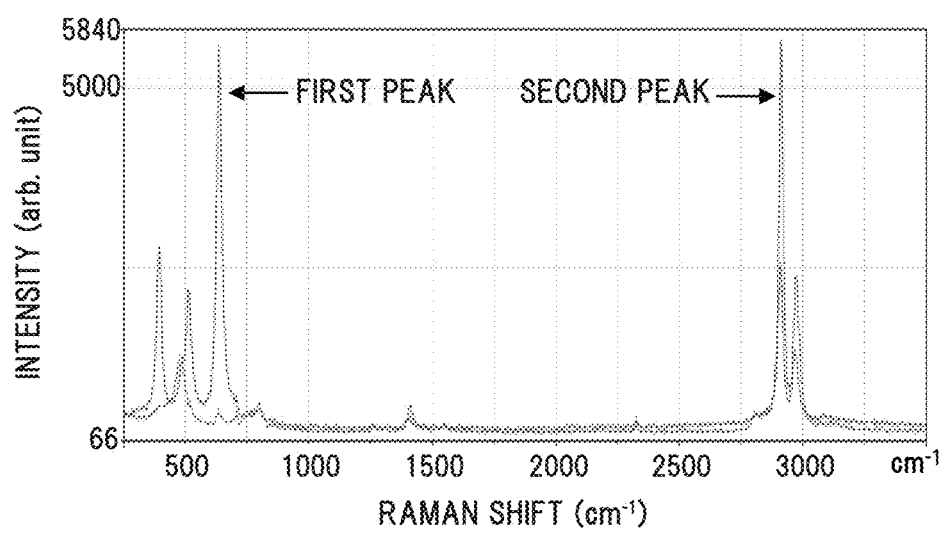
FIG. 9 is a graph showing the Raman scattering spectrum measured at a point in sample E1.
Figure 10A:
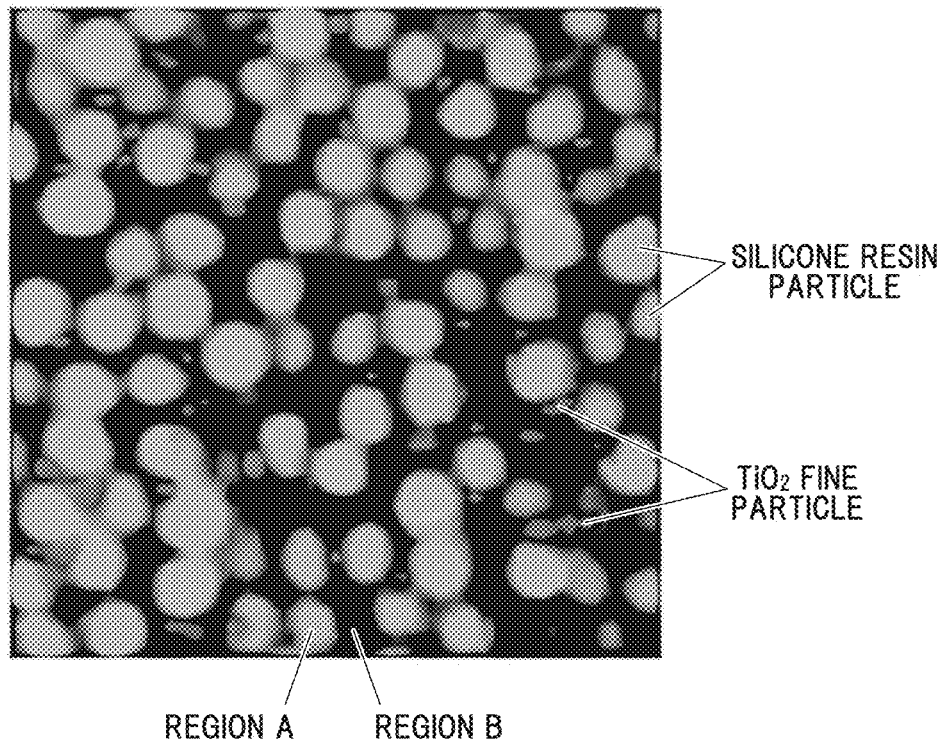
FIG. 10A is a diagram showing the mapping image of the sample E1 obtained by mapping analysis.
Figure 10B:
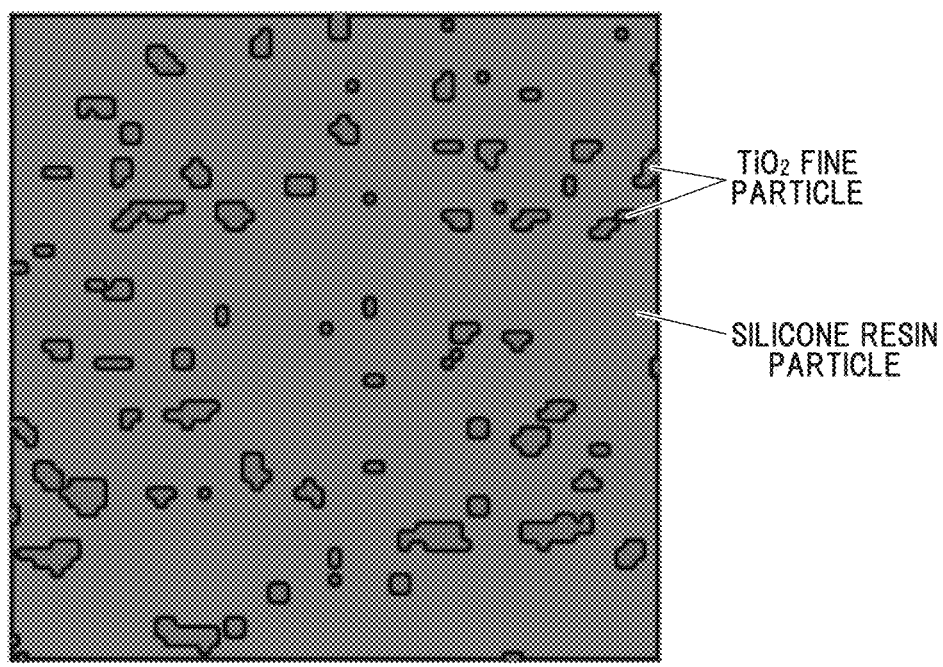
FIG. 10B is a diagram showing bivaluated analysis image of the mapping image in FIG. 10A.
Figure 11A:
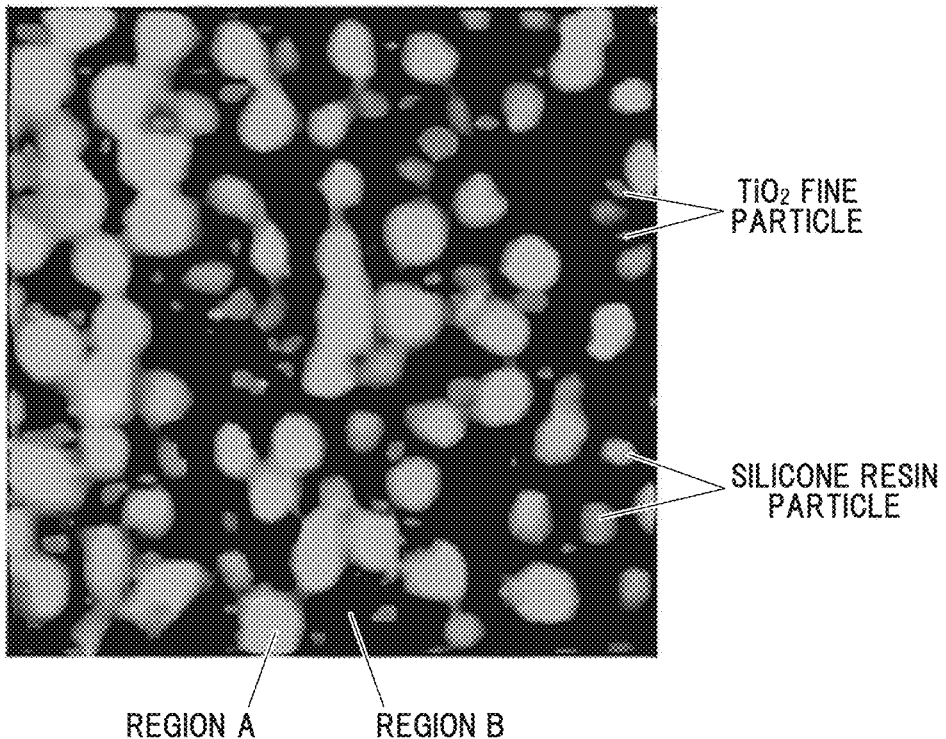
FIG. 11A is a diagram showing a mapping image of sample E2 obtained by mapping analysis.
Figure 11B:
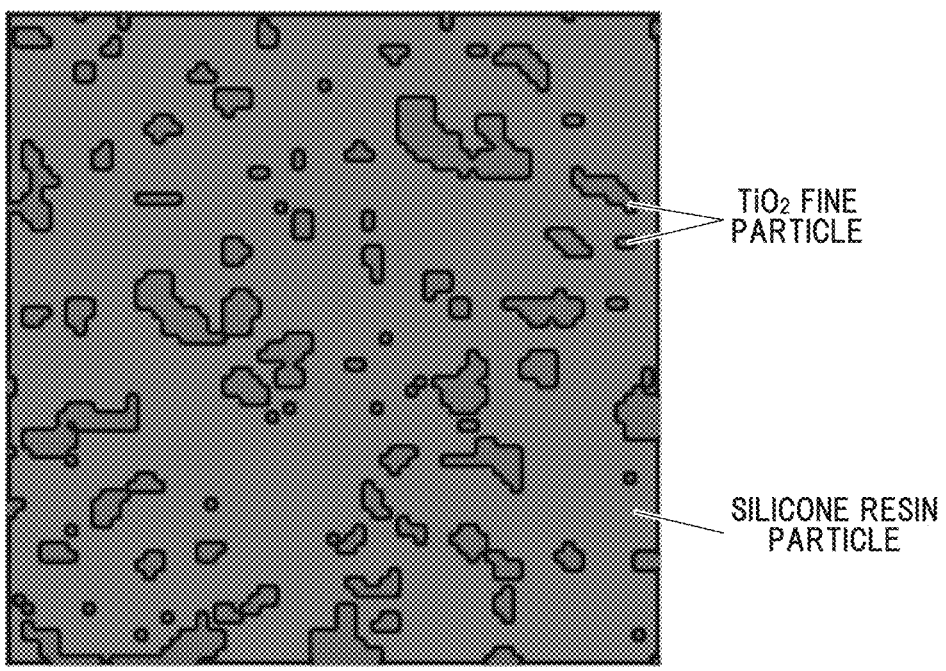
FIG. 11B is a diagram showing a bivaluated analysis image of the mapping image in FIG. 11A.
Figure 12A:
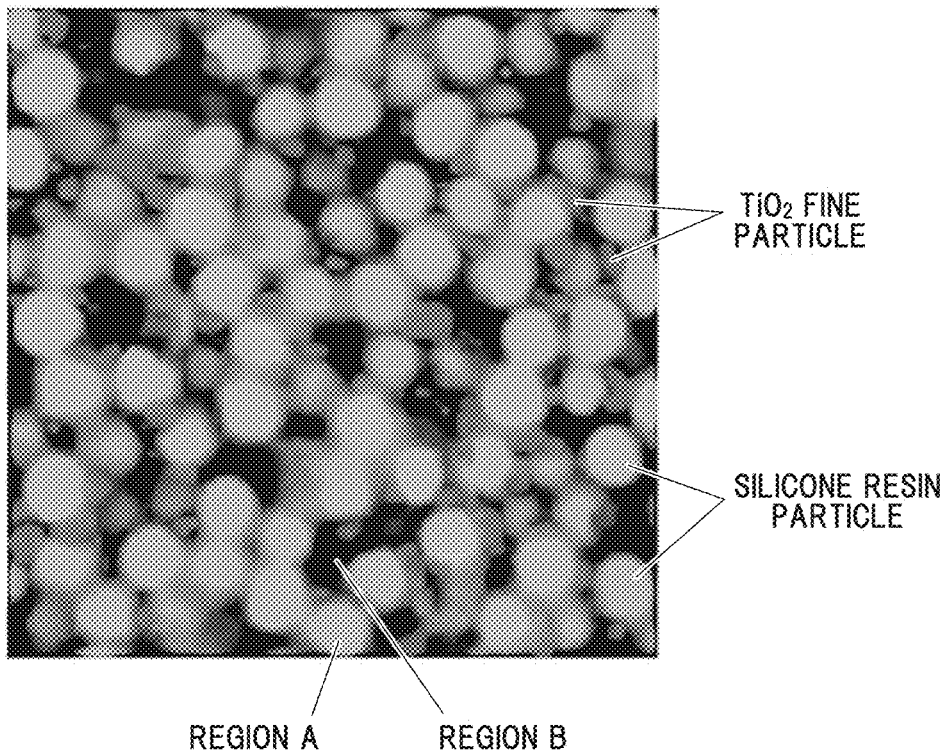
FIG. 12A is a diagram showing the mapping image of sample E3 obtained from mapping analysis.
Figure 12B:
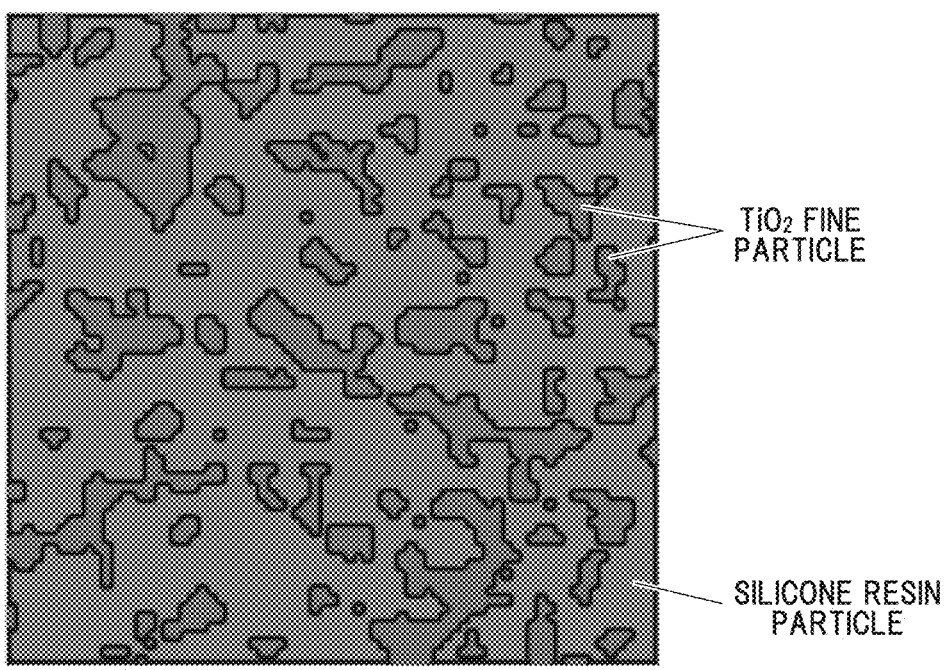
FIG. 12B is a diagram showing a bivaluated analysis image of the mapping image in FIG. 12A.
Figure 13A:
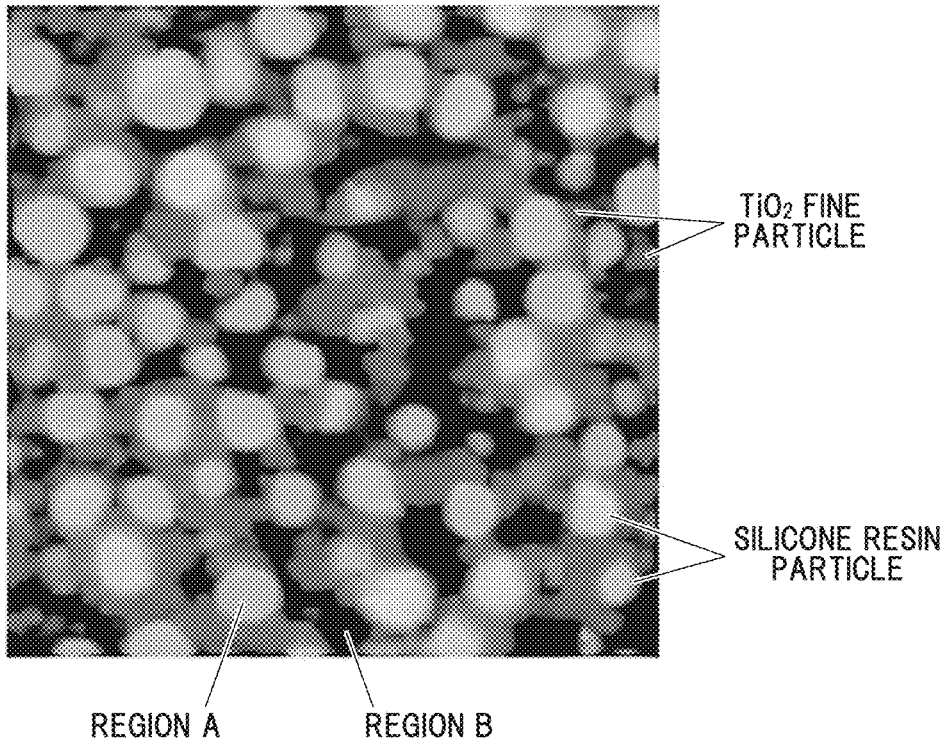
FIG. 13A is diagram showing a mapping image of the sample E4 obtained by mapping analysis.
Figure 13B:
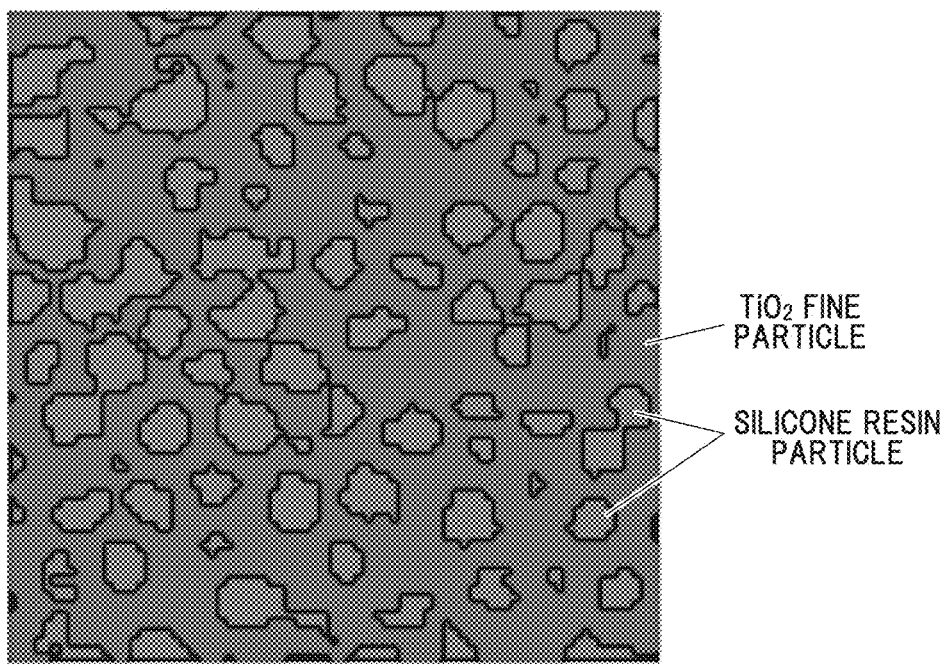
FIG. 13B is a diagram showing bivaluated analysis image of the mapping image in FIG. 13A.

FIG. 9 shows an example of the Raman scattering spectrum collected at a point in the sample E1. The peak at approximately 640 cm$^{-1}$ (e.g., 640+/−20 cm$^{-1}$) (Hereinafter referred to as "the first peak") in the Raman scattering spectrum is a particularly strong peak in the scattering spectrum of titanium oxide fine particles (mainly including anatase-type TiO$_2$ fine particles), mainly derived from lattice vibration Eg of the anatase-type TiO$_2$. The peak at 2915+/−33 cm$^{-1}$ (Hereinafter referred to as "the second peak") is a particularly strong peak in the scattering spectrum of the silicone resin, which is derived from the CH stretch of the silicone resin. In the Raman mapping analysis for this example, the intensities of these first and second peaks were used to map the distribution of titanium oxide fine particles and silicone resin fine particles. If titanium oxide fine particles mainly include rutile type TiO$_2$ fine particles, it is preferable to use a peak at approximately 445 cm$^{-1}$ (e.g., 445+/−45 cm$^{-1}$) derived from lattice vibration Eg as the first peak. Also, if titanium oxide fine particles mainly include brookite-type TiO$_2$ fine particles, it is preferable to use a peak at approximately 150 cm$^{-1}$ (e.g., 150+/−15 cm$^{-1}$) as the first peak.

FIGS. 10A, 11A, 12A, and 13A are respectively mapping images of the samples E1, E2, E3 and E4 obtained from the mapping analysis. The size of each mapping image (the mapping area) is 22.5 μm×22.5 μm.

The mapping analysis was performed using the analysis software Raman Viewer Ver. 4.5.54 made by Nanophoton Corporation. The tint in the area representing the titanium oxide fine particles in FIGS. 10A, 11A, 12A, and 13A was set within the range of intensity of 20 to 3500 in such a manner that the tint should be darker as the intensity of the first peak increases. Further, the tint was set in such a manner that the titanium oxide fine particles should be present for the values within the range of 1760 to 3500. In addition, the tint in the area representing the silicone resin fine particles was set within the range of intensity of 400 to 3000 in such a manner that the tint should be darker as the intensity of the second peak increases. Further, the tint was set in such a manner that the silicone resin fine particles should be present for the values within the range of 1700 to 3000. An area where neither Raman peak showing silicone resin fine particles nor Raman peak showing titanium oxide fine particles are observed, i.e., area of the silicone rubber as the base material 111 is observed with a different color from those areas.

According to FIGS. 10A, 11A, 12A, and 13A, the titanium oxide fine particles are polarized around the silicone resin fine particle. It can be seen that the area without silicone resin fine particles (the area located between the silicone resin fine particles) is effectively filled. This is because the average particle size of the titanium oxide fine particles is smaller than the average particle size of the silicone resin fine particles (for example, ½ or less, preferably ⅕ or less). In addition, as the amount of titanium oxide fine particles increases, the proportion of the area occupied by titanium oxide fine particles in areas where silicone resin fine particles are not present increases, and when the Ti concentration is 1.5 mass % or more, almost all areas in the area where silicone resin fine particles are not present (areas that are less resistant to UV-C light) are occupied by titanium oxide fine particles.

Namely, the second layer 11 includes a region where the intensity of the first peak in the area where silicone resin fine particles are present (a circular white region: Region A in FIGS. 10A, 11A, 12A and 13A) is less than the intensity of the first peak in the area where silicone resin fine particles are not present (a region located between the silicone resin fine particles: Region B), since titanium oxide fine particles are present predominantly in the area where silicone resin fine particles are not present. In this way, in the second layer 11, titanium oxide fine particles are not evenly distributed, and titanium oxide fine particles are polarized around a silicone resin fine particle.

FIGS. 10B, 11B, 12B, and 13B, respectively, show bivaluated analysis images of the mapping images in FIGS. 10A, 11A, 12A, and 13A.

This bivaluated analysis was performed by the "area ratio analysis" function of the above analysis software, Raman Viewer Ver. 4.5.54. In this bivalation analysis, an integral intensity of an integral range of 38.7 cm$^{-1}$ at the first peak was applied to calculation as a first peak intensity, and an integral intensity of an integral range of 35.2 cm$^{-1}$ at the second peak was applied to the calculation as a second peak intensity. In the Raman Viewer Ver. 4.5.54, the intensity calculation method for the bivaluated analysis is called "area calculation".

According to the bivaluated analysis images shown in FIGS. 10B, 11B, 12B, and 13B, a ratio of the area of titanium oxide fine particles to the area other than titanium oxide fine particles (i.e., total area of silicone resin fine particles and silicone rubber) is 6.4:93.6, 12.8:87.2, 22.7:77.3, and 35.2:64.8, respectively.

Based on the above results, it is found that when the ratio of the area of titanium oxide fine particles to the total area of titanium oxide fine particles and silicone resin fine particles in the bivaluated analysis image conducted under the above conditions is 22.7% or more, almost all areas in the area where silicone resin fine particles are not present are occupied by titanium oxide fine particles, and that the second layer 11 has excellent resistance to UV-C light. The conditions for this second layer 11 to have excellent resistance to UV-C light would be satisfied even if the silicone resin fine particle as the first fine particle 112 is changed to another fine particle such as silica fine particle, or if the titanium oxide fine particle as the second fine particle 113 is changed to another fine particle such as carbon particle. In order to reduce the static friction coefficient, it is necessary to have an area where some silicone resin fine particles are present. Therefore, it is preferable that the upper limit of the area of titanium oxide fine particles in the bivaluated analysis image is not less than 50% relative to the total area of titanium oxide fine particles and silicone resin fine particles.

Example 3

(Preparation of the Laminate Structure 1)

Eleven samples (samples C1 to C11) were prepared to verify the resistance of the laminate structure 1 to UV-C light. All the samples C1 to C11 have the first layer 10 and the second layer 11, and the first layer 10 includes $TiO_2$ fine particles 102. Of the samples C1 to C11, the samples C1, C6, and C9 do not include $TiO_2$ fine particles 113 in the second layer 11 and were prepared using processes and materials similar to the sample A3 in Example 1. Also, the samples C2 to C5, C7, C8, C10, C11 include $TiO_2$ fine particles 113 in the second layer 11 (Ti concentration is within range from 1.1 mass % to 4.4 mass %) and were prepared using processes and materials similar to the sample A4 in Example 1. Table 5 below shows the composition of the sheath 23 and the coating film 24 of the samples C1 to C11. The thickness of the first layer 10 (sheath 23) was 0.8 mm, and the thickness of the second layer 11 (coating film 24) was 20 μm.

(Verification of UV-C Light Resistance)

In order to verify the resistance of the laminate structure 1 to UV-C light from the viewpoint of the strength to bending, a bending test equivalent to 45% to 50% tensile for the samples C1 to C11 after exposure to UV-C light was conducted. UV-C light irradiation was performed by a storage chamber with sterilization lamps (Storage chamber DM-5, lamps GL-10, available from Daishin Kogyo Co., Ltd.) at chamber temperature of 25 to 40° C., chamber humidity of 28% to 65%, chamber pressure of 1 atm (atmospheric pressure), wavelength 253.7 nm, illuminance of 1.3 mW/cm$^2$, and irradiation times of 200, 300, 400, and 600 hours. The illuminance meter was UVC-254A made by MK Scientific Inc. The bending test was also performed on the samples C1 to C11 at an ambient temperature of 15 to 35° C. and an ambient humidity of 28 to 65% under atmospheric pressure.

Figure 14A:
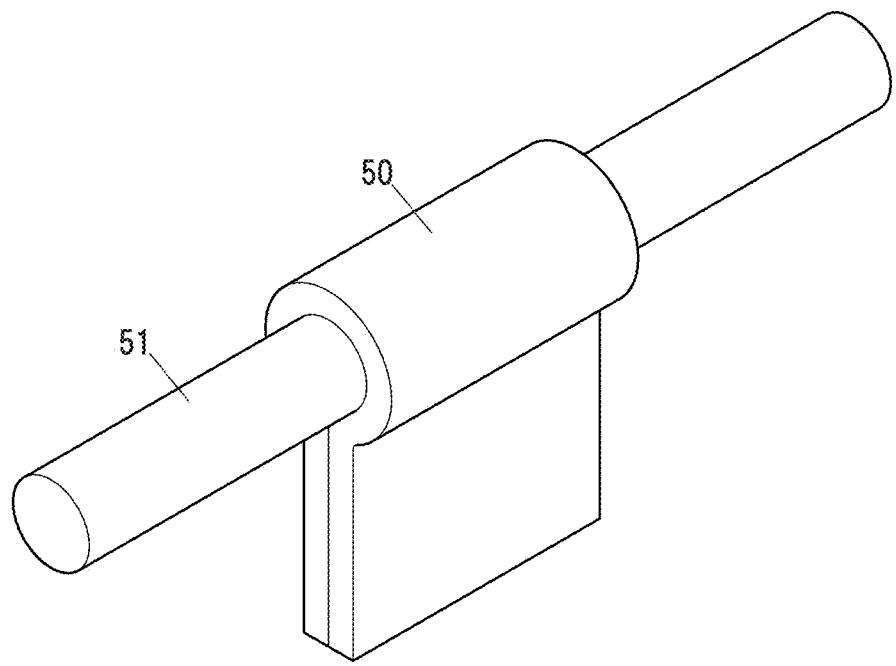
FIG. 14A is a schematic diagram showing the bending test.

FIG. 14A shows a schematic diagram of the bending test. A sheath piece 50 was a part of the sheath 23 covered with the coating film 24, cut from each of the samples C1 to C11. In the bending test, a rectangular sheath piece 50 is cut from each of the samples C1 to C11 and wrapped around a lead wire (metal wire) 51 having a radius of 0.5 mm, then overlapping portions of the sheath piece 50 are fixed by pinching them from both sides (a fixing jig is not shown). Here, cable-shape samples C1 to C11 of a length of 1 m were prepared and cut evenly along the cable length from ten locations to provide each piece with a size of 12 mm (in a cable circumferential direction)×18 mm (in a cable longitudinal direction). The sheath piece 50 was wrapped around the lead wire 51 in such a manner that a cable longitudinal

TABLE 5

| | Sheath 23 | | Coating film 24 | | |
|---|---|---|---|---|---|
| | Parent material 101 | TiO$_2$ fine particle 102 | Parent material 111 | Fine particle 112 | TiO$_2$ fine particle 113 |
| C1 | Silicone rubber | Anatase TiO$_2$ (Ti: 0.12 mass %) | Silicone rubber | Average particle size 5 μm Silicone resin | None |
| C2 | Silicone rubber | Anatase TiO$_2$ (Ti: 0.12 mass %) | Silicone rubber | Average particle size 5 μm Silicone resin | Anatase TiO$_2$ (Ti: 1.1 mass %) |
| C3 | Silicone rubber | Anatase TiO$_2$ (Ti: 0.12 mass %) | Silicone rubber | Average particle size 5 μm Silicone resin | Anatase TiO$_2$ (Ti: 1.5 mass %) |
| C4 | Silicone rubber | Anatase TiO$_2$ (Ti: 0.12 mass %) | Silicone rubber | Average particle size 5 μm Silicone resin | Anatase TiO$_2$ (Ti: 1.9 mass %) |
| C5 | Silicone rubber | Anatase TiO$_2$ (Ti: 0.12 mass %) | Silicone rubber | Average particle size 5 μm Silicone resin | Anatase TiO$_2$ (Ti: 4.4 mass %) |
| C6 | Silicone rubber | Anatase TiO$_2$ (Ti: 0.6 mass %) | Silicone rubber | Average particle size 5 μm Silicone resin | None |
| C7 | Silicone rubber | Anatase TiO$_2$ (Ti: 0.6 mass %) | Silicone rubber | Average particle size 5 μm Silicone resin | Anatase TiO$_2$ (Ti: 1.5 mass %) |
| C8 | Silicone rubber | Anatase TiO$_2$ (Ti: 0.6 mass %) | Silicone rubber | Average particle size 5 μm Silicone resin | Anatase TiO$_2$ (Ti: 1.9 mass %) |
| C9 | Silicone rubber | Anatase TiO$_2$ (Ti: 1.1 mass %) | Silicone rubber | Average particle size 5 μm Silicone resin | None |
| C10 | Silicone rubber | Anatase TiO$_2$ (Ti: 1.1 mass %) | Silicone rubber | Average particle size 5 μm Silicone resin | Anatase TiO$_2$ (Ti: 1.5 mass %) |
| C11 | Silicone rubber | Anatase TiO$_2$ (Ti: 1.1 mass %) | Silicone rubber | Average particle size 5 μm Silicone resin | Anatase TiO$_2$ (Ti: 1.9 mass %) | side would be located along a circumferential direction of the lead wire 51 and the second layer 11 would be located on an outer periphery side.

Figure 14B:
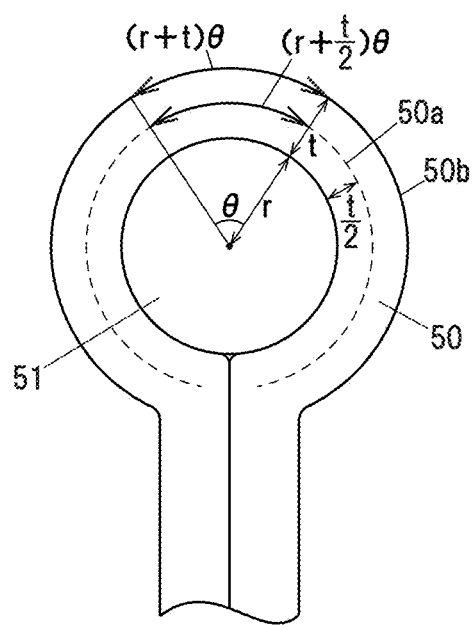
FIG. 14B is a cross-sectional view of a lead wire and a sheath piece wrapped around the lead wire.

FIG. 14B shows a cross-sectional view of the lead wire 51 and the sheath piece 50 wrapped around the lead wire 51. If the radius of the lead wire 51 is r and the thickness of sheath piece 50 is t, a longitudinal length of the sheath piece 50 at a neutral surface 50$a$ at any angle $\theta$ is $(r+t/2)\cdot\theta$, and a longitudinal length of an outer surface 50$b$ of the sheath piece 50 is $(r+t)\cdot\theta$, as shown in FIG. 14B. Therefore, a longitudinal elongation rate of the outer surface 50$b$ of the sheath piece 50 wrapped around the lead wire 51 is expressed as $\{(r+t)\cdot\theta-(r+t/2)\cdot\theta\}/((r+t/2)\cdot\theta)\times100=t/(2r+t)\times100$, and the radius r of the lead wire 51 is 0.5 mm and the thickness t of the sheath piece 50 is 0.82 mm, so that the longitudinal elongation rate is approximately 45%.

The bending test was performed on the sheath pieces 50 cut from the samples C1 to C11. The surface of the sheath piece 50 during the bending test (the second layer 11 was affected by an elongation equivalent to 45% to 50%) was observed with a 50× magnification ratio using an optical microscope (Digital Microscope VHX-1000 made by Keyence Corporation). As a result, for the sheath pieces 50 of the samples C1, C6, and C9 that did not include TiO$_2$ fine particles in the second layer 11, no cracks occurred on the surface of the sample when being exposed to UV-C light at irradiation energy (intensity (W/cm$^2$)×irradiation time (seconds)) of 936 J/cm$^2$, but cracks occurred on the surface of the sample when being exposed to UV-C light at irradiation energy of 1404 J/cm2, 1872 J/cm2, and 2808 J/cm2.

On the other hand, for the sheath pieces 50 cut from the samples C2 to C5, C7, C8, C10, and C11 including TiO$_2$ fine particles in the second layer 11, no cracks occurred on the surface of the sample being exposed to UV-C light at irradiation energy of 936 J/cm$^2$, 1404 J/cm$^2$, 1872 J/cm$^2$, and 2808 J/cm$^2$. In this bending test, the term "crack" refers to a recess that reaches from the second layer 11 (coating film 24) of the first layer 10 (sheath 23).

Figure 15A:
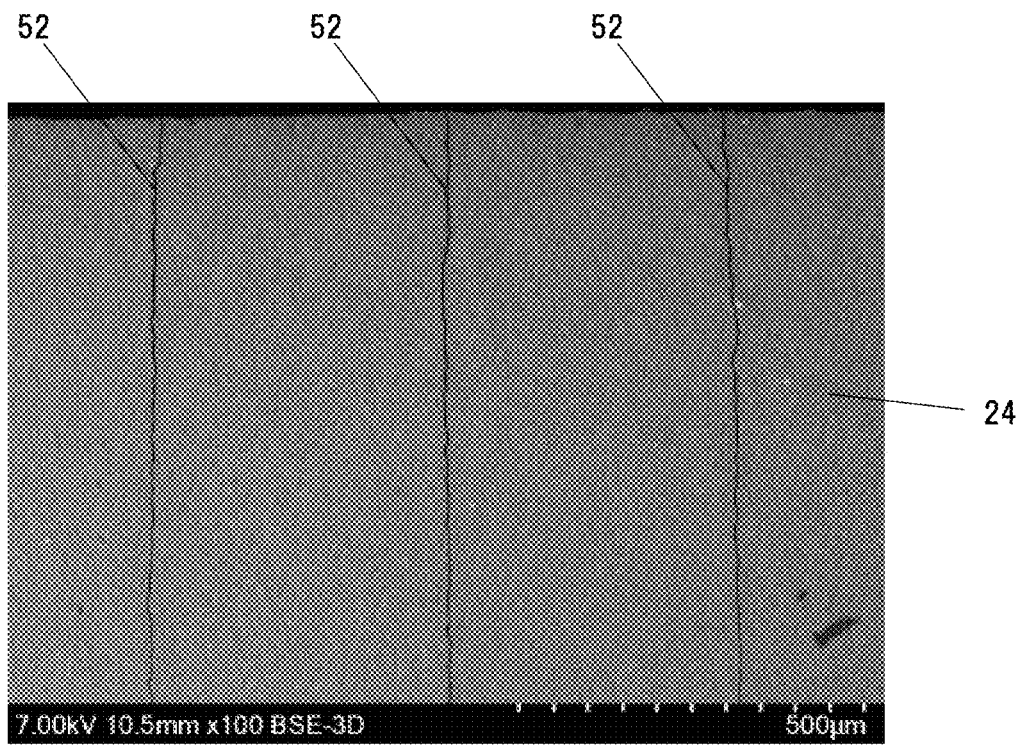
FIGS. 15A and 15B are SEM observation images of a surface and a cross section of the sheath piece cut from sample C6 exposed to UV-C light with irradiation energy of 2808 J/cm$^2$.
Figure 15B:
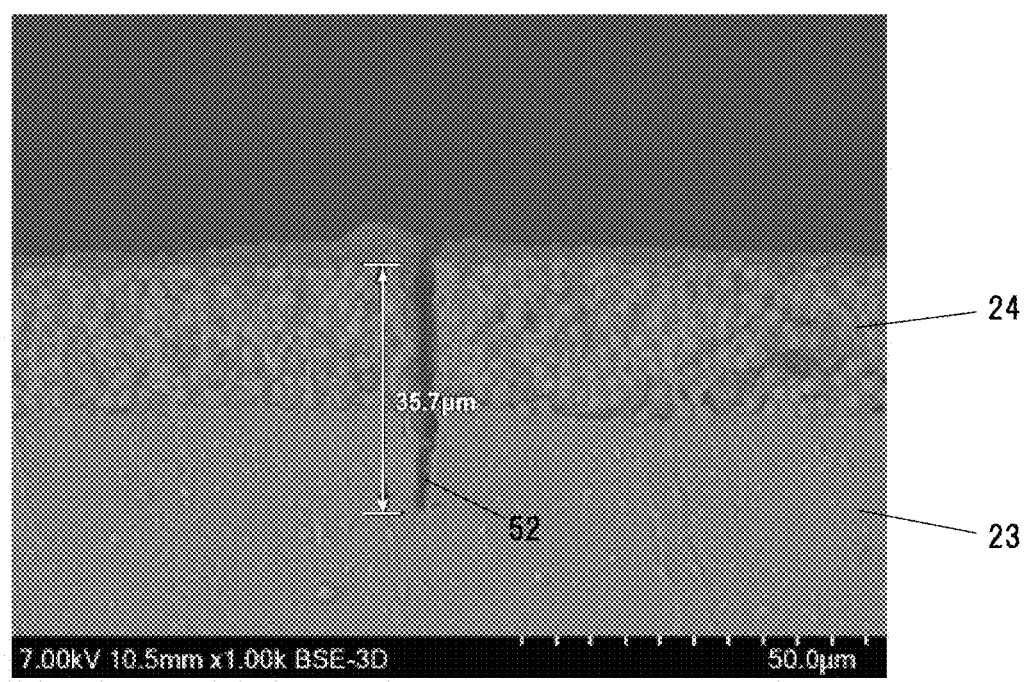
Figure 16A:
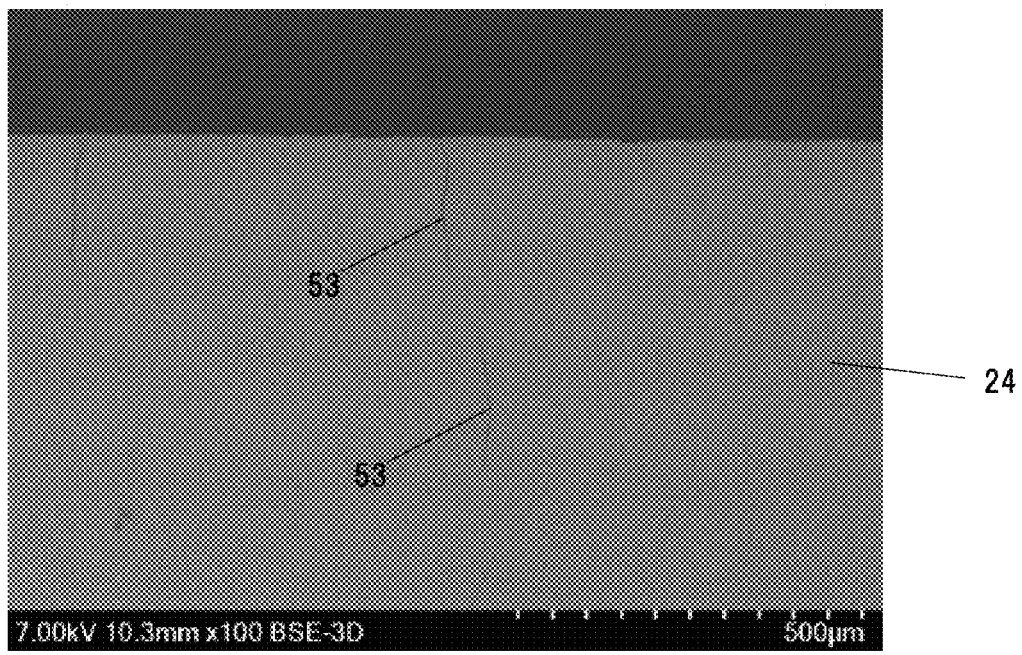
FIGS. 16A and 16B are SEM observation images of a surface and a cross section of a sheath piece cut from sample C7 exposed to UV-C light with an irradiation energy of 2808 J/cm$^2$.
Figure 16B:
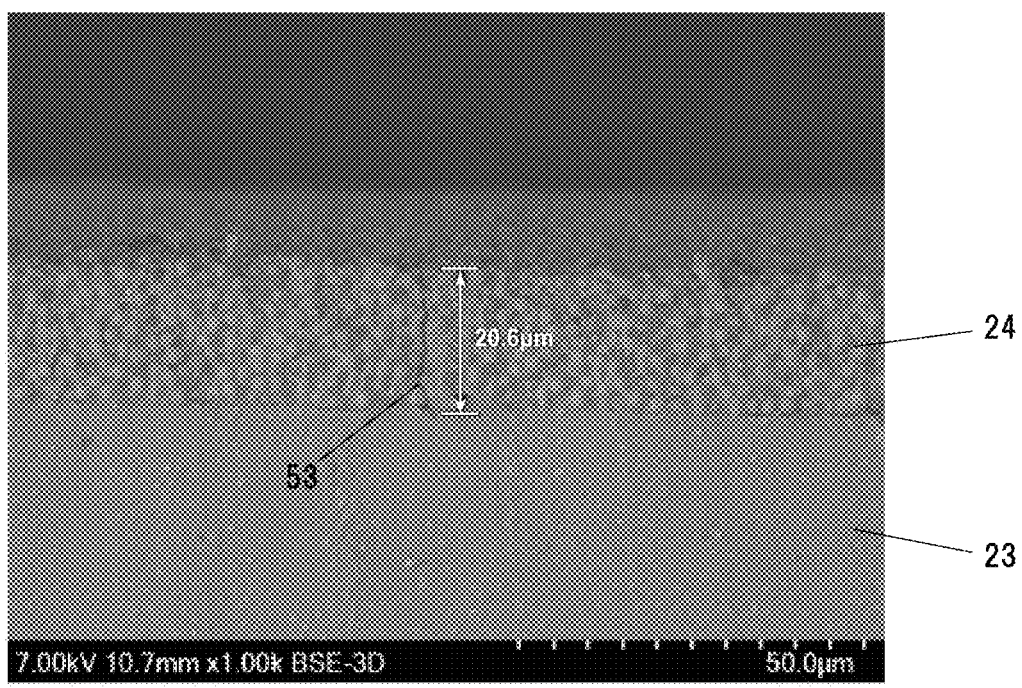
Figure 18A:
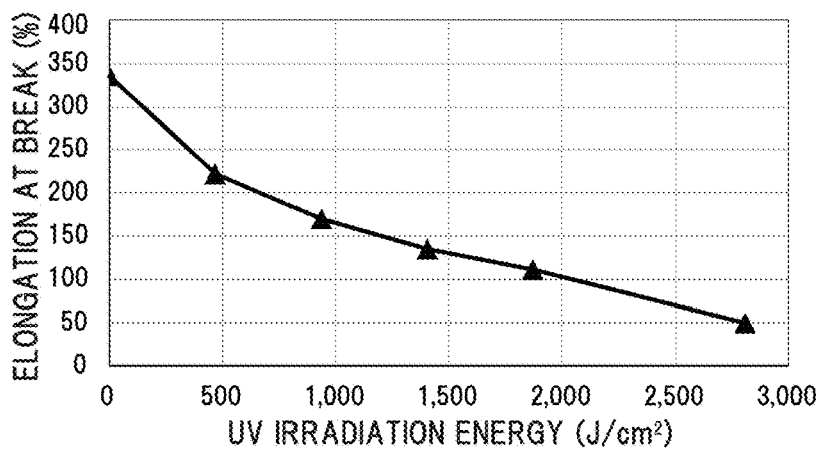
FIGS. 18A, 18B, 18C and 18D are graphs showing the relationship between the irradiation energy of UV-C light and the elongation at break for samples D1, D3, D4, and D7, respectively.
Figure 18B:
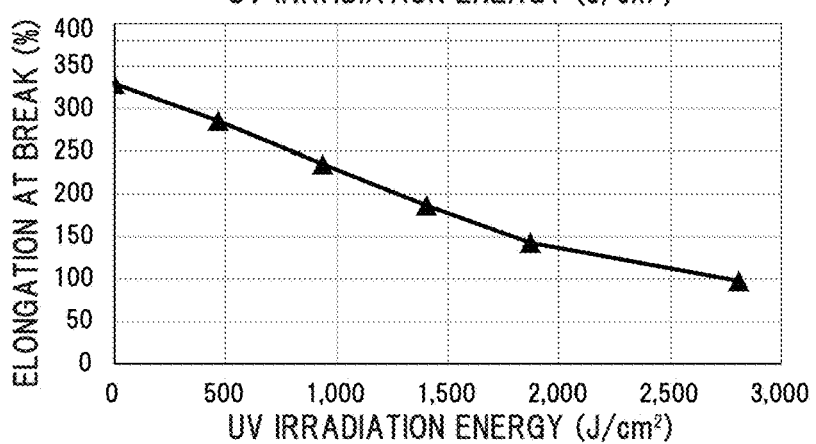
Figure 18C:
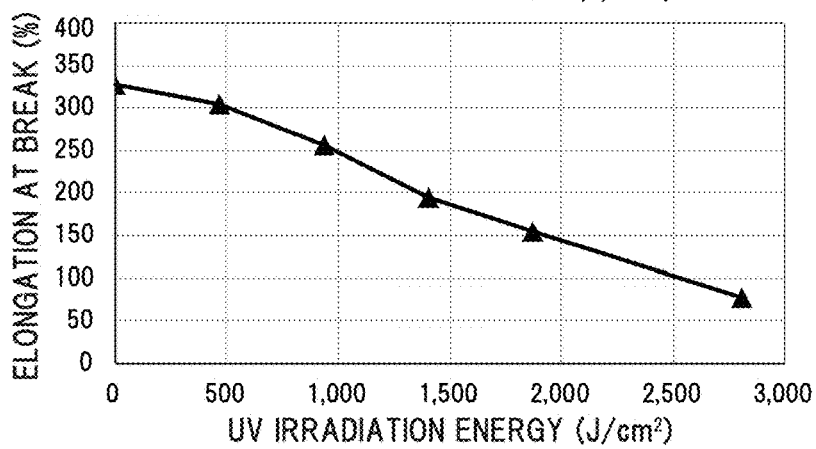
Figure 18D:
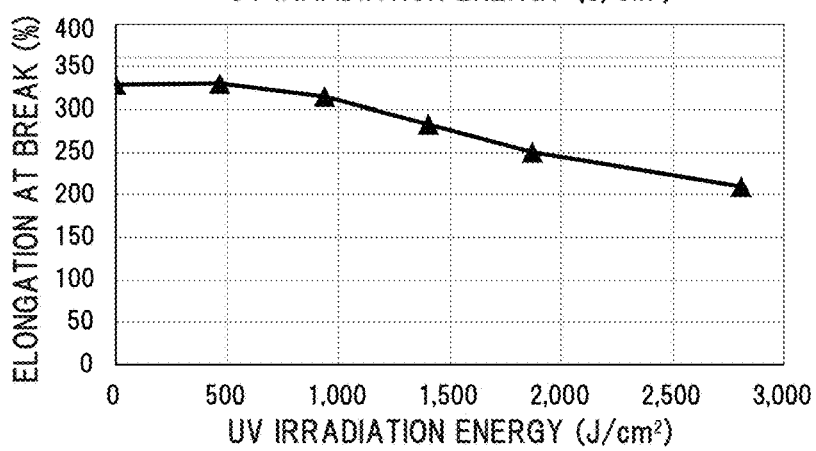
Figure 19A:
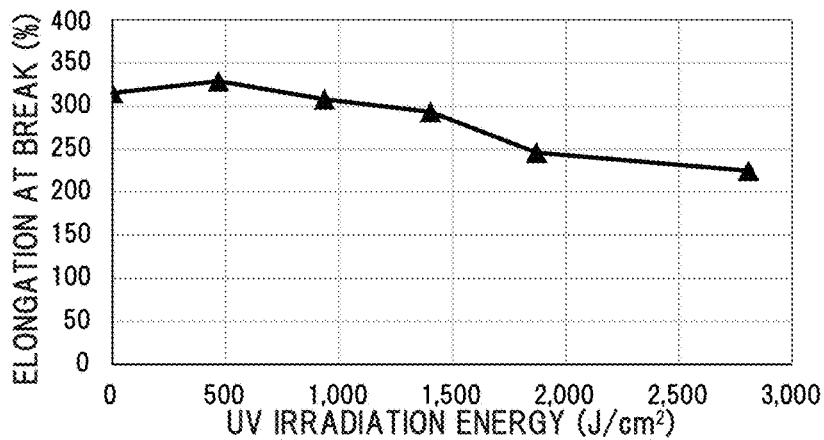
FIGS. 19A, 19B, 19C and 19D are graphs showing the relationship between the irradiation energy of UV-C light and the elongation at break for samples D8, D9, D10, and D11, respectively.
Figure 19B:
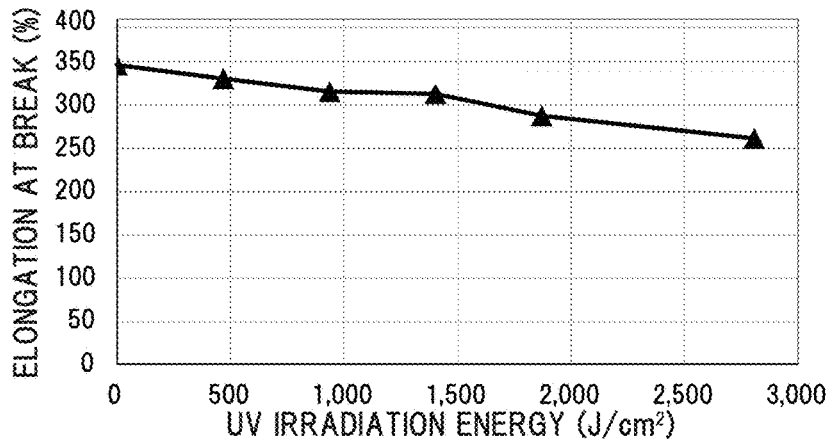
Figure 19C:
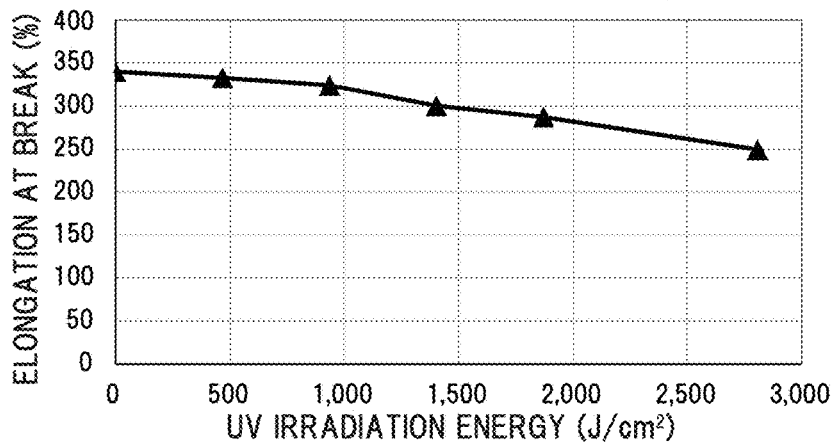
Figure 19D:
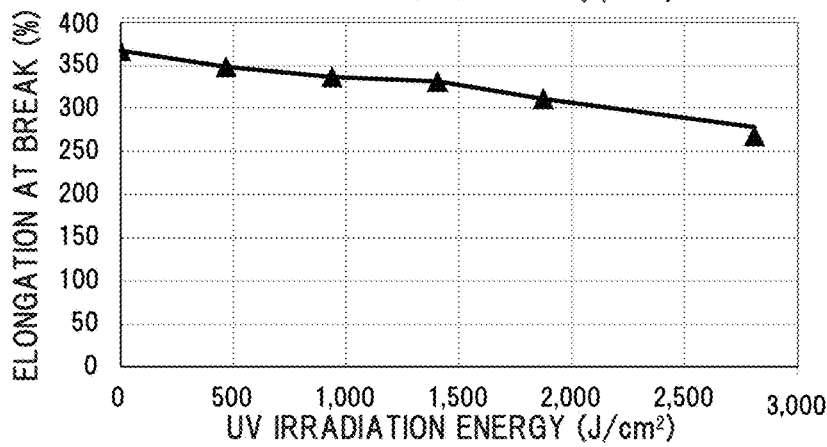

FIGS. 15A and 15B show SEM observation images of a surface and a cross section of the sheath piece 50 cut from the sample C6 exposed to UV-C light at irradiation energy of 2808 J/cm$^2$. FIGS. 16A and 16B show SEM observation images of the surface and a cross section of the sheath piece 50 cut from the sample C7 exposed to UV-C light with irradiation energy of 2808 J/cm$^2$. In the SEM observation images in FIGS. 15A and 15B, cracks 52 that reach the second layer 11 to the first layer 10 were observed. On the other hand, the recess 53 observed in the SEM observation images in FIGS. 16A and 16B did not reach the first layer 10 and was not counted as a crack. FIGS. 15A and 16A are 100×SEM observation images, and FIGS. 15B and 16B are 1000×SEM observation images. They are the SEM observation image of the sheath piece 50 which was removed from the lead wire 51 after the bending test.

In addition, the results of this bending test were used as one of the criteria for determining whether the laminate structure 1 is resistant to UV-C light. The sheath pieces 50 were taken from ten locations of each sample exposed to UV-C light. The bending test was conducted on each of ten sheath pieces 50, the number of sheath pieces 50 on which the cracks were observed was counted when observing the area of 1.5 mm×4.5 mm using an optical microscope to obtain a 50× magnification ratio. When the areas of 1.5 mm×4.5 mm at ten locations of the sample were observed and the number of the areas of 1.5 mm×4.5 mm in which the cracks were observed is 3 or less, the laminate structure 1 was determined to be resistant to UV-C light.

Figure 17:
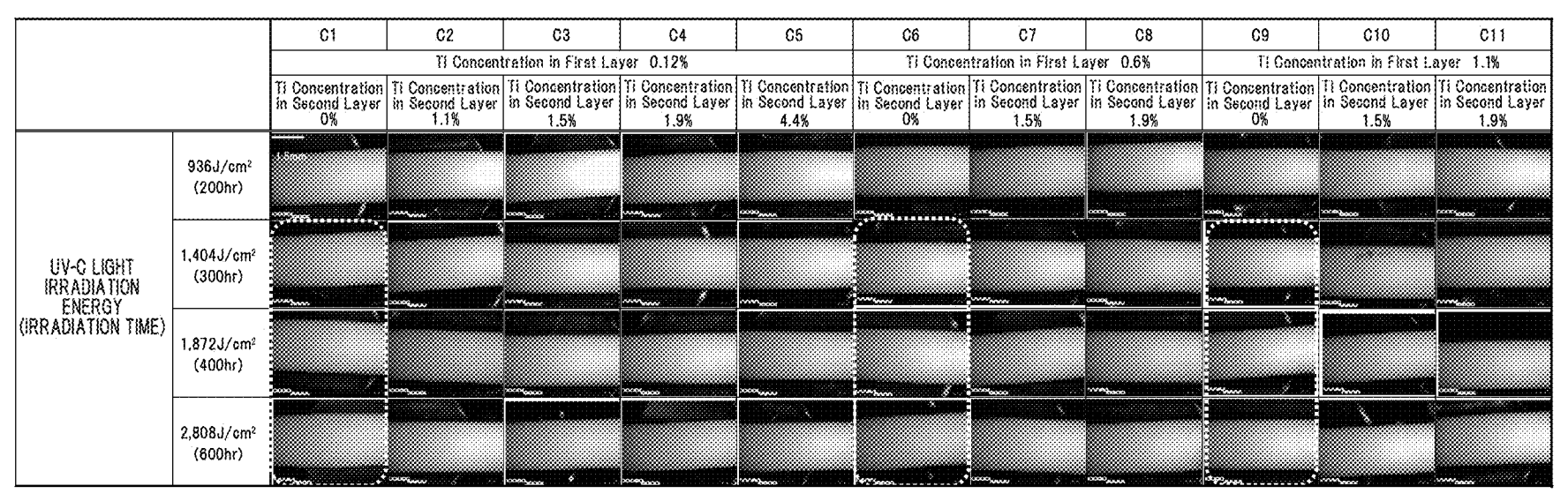

FIG. 17 shows a representative observation image of the surface of the sheath piece 50 when the bending test was performed on the sheath pieces 50 cut from the samples C1 to C11. The observation image in FIG. 17 is an image of an area of 1.5 mm×4.5 mm on the surface of the sheath piece 50 prepared from the samples C1 to C11, which was observed with a 50× magnification using an optical microscope (Digital Microscope VHX-1000 made by Keyence Corporation). According to FIG. 17, cracks are observed on the surface of each of the sheath pieces 50 of the samples C1, C6, and C9 that do not include TiO$_2$ fine particles in the second layer 11, after being exposed to UV-C light at irradiation energy (intensity (W/cm$^2$)×irradiation time (seconds)) of 1404 J/cm$^2$, 1872 J/cm$^2$, and 2808 J/cm$^2$. For the sheath pieces 50 cut from the samples C2 to C5, C7, C8, C10, and C11 including TiO$_2$ fine particles in the second layer 11, no cracks occurred on any surface of the samples exposed to UV-C light with irradiation energy of 936 J/cm$^2$, 1404 J/cm$^2$, 1872 J/cm$^2$, and 2808 J/cm$^2$.

For example, a thread-like pattern along the sample longitudinal direction was observed in the samples C10 and C11 after irradiation at 2808 J/cm$^2$. This pattern is a recess that did not reach the sheath 23 and appeared only in the coating film 24. In other words, the thickness of the coating film 24 is greater than the depth of the recess. Such a recess is not counted as a crack, as described above, because it does not serve as the starting point for the breaking of the sheath 23. It is also possible to determine whether the thread-like pattern is a crack or not by observing whether this pattern has reached the sheath 23 or not from the cross-sectional SEM observation images shown in FIGS. 15B and 16B.

From the results in FIG. 17, for the samples C2 to C5, C7, C8, C10, and C11, the number of the areas of 1.5 mm×4.5 mm in which the cracks were observed is 3 or less among 10 locations (specifically, 0 (no cracks)), and these samples were found to be resistant to UV-C light. In addition, for the samples C1, C6, and C9, the number of the areas of 1.5 mm×4.5 mm in which the cracks were observed is 4 or more among 10 locations, and these samples were found to not be resistant to UV-C light. Thus, it was found that increasing the content of the TiO$_2$ fine particles in the second layer 11 is effective in suppressing cracks in the laminate structure 1. Specifically, it was confirmed that cracking of the laminate structure 1 could be suppressed by setting the Ti concentration in the second layer 11 to 1.0 mass % or more.

Next, to verify the resistance of the laminate structure 1 to UV-C light from the degree of elongation at break, a tensile test was performed on the samples C1 to C5 and C7 to C11 after UV-C light exposure. UV-C light irradiation was performed by a storage chamber with sterilization lamps (Storage chamber DM-5, lamps GL-10, available from Daishin Kogyo Co., Ltd.) at chamber temperature of 25 to 40° C., chamber humidity of 28% to 65%, chamber pressure of 1 atm (atmospheric pressure), wavelength 253.7 nm, illuminance of 1.3 mW/cm$^2$, and irradiation times of 100, 200, 300, 400, and 600 hours.

After being exposed to UV-C light, dumbbell test pieces D1 to D5 and D7 to D11 were respectively prepared from the cable-like samples C1 to C5 and C7 to C11, in a similar way to the method used to prepare the samples B1 to B4 from the samples A1 to A4 in Example 1. The tensile test for the samples D1 to D5 and D7 to D11 (Dumbbell test piece No. 6) was performed in the same way and conditions as the test prescribed in "JIS K6251 (1994)" for the samples B1 to B4. At the tensile test evaluation site, an ambient temperature was 25+/−3° C., an ambient humidity was 50+/−10%, and a pressure was atmospheric pressure. The distance between the marks was 20 mm and the tensile speed was 500 mm/min, leading to a break.

FIGS. 18A, 18B, 18C and 18D are graphs showing the relationship between an irradiation energy (intensity (W/cm$^2$)×irradiation time (seconds)) of UV-C light and the degree of elongation at break for the samples D1, D3, D4, and D7, respectively. FIGS. 19A, 19B, 19C, and 19D are graphs showing the relationship between an irradiation energy of UV-C light and the degree of elongation at break for the samples D8, D9, D10, and D11, respectively. Table 6 below shows the numerical values of the plotting points in FIGS. 18A, 18B, 18C, 18D, 19A, 19B, 19C, and 19D, i.e., the elongation at break (%) for each irradiation energy of UV-C light in each sample.

TABLE 6

| | UV-C light irradiation energy (J/cm$^2$) | | | | | |
|---|---|---|---|---|---|---|
| | 0 | 468 | 936 | 1404 | 1872 | 2808 |
| D1 | 335.8 | 222.3 | 170.0 | 135.0 | 111.2 | 49.9 |
| D3 | 329.4 | 285.8 | 235.1 | 186.6 | 142.7 | 97.7 |
| D4 | 327.4 | 304.3 | 256.2 | 194.6 | 154.6 | 77.3 |
| D7 | 329.1 | 330.4 | 315.1 | 283.0 | 250.2 | 209.7 |
| D8 | 315.1 | 328.7 | 307.8 | 293.1 | 245.8 | 224.7 |
| D9 | 347.0 | 331.1 | 316.0 | 313.5 | 287.9 | 261.7 |
| D10 | 340.0 | 332.7 | 324.0 | 300.2 | 287.1 | 249.2 |
| D11 | 367.3 | 348.4 | 336.7 | 331.4 | 311.2 | 278.2 |

According to FIGS. 18A to 18D, 19A to 19D, and Table 6, the elongation at break of the samples D7 to D11 of the elongation at break of the samples D1, D3, D4 and D7 to D11 is 250% or more, even when the elongation at break of the samples D7 to D11 is 1404 J/cm$^2$, and it is confirmed that the samples D7 to D11 have high resistance to UV-C light from the viewpoint of the elongation at break. Also, the elongation at break of the samples D7 to D11 of the elongation at break of the samples D1, D3, D4 and D7 to D11 is 200% or more, even when the elongation at break of the samples D7 to D11 is 1872 J/cm$^2$, and it is confirmed that the samples D7 to D11 have high resistance to UV-C light from the viewpoint of the elongation at break. Further, the elongation at break of the samples D7 to D11 of the elongation at break of the samples D1, D3, D4 and D7 to D11 is 150% or more, even when the elongation at break of the samples D7 to D11 is 2808 J/cm$^2$, and it is confirmed that the samples D7 to D11 have high resistance to UV-C light from the viewpoint of the elongation at break.

Figure 20A:
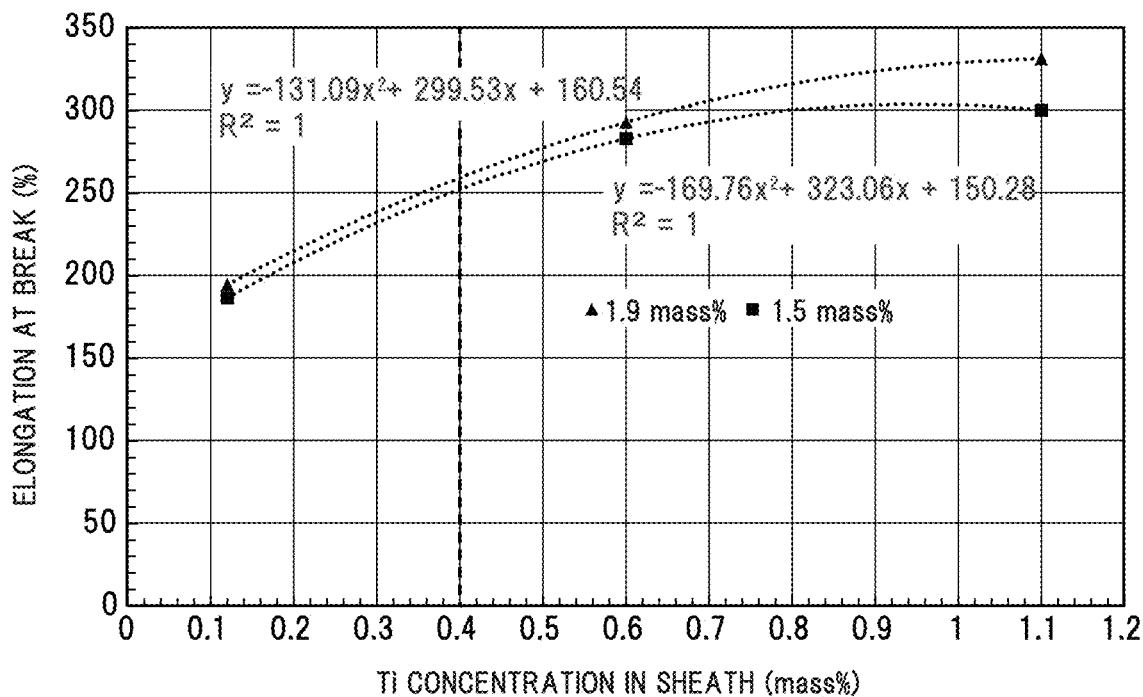
FIGS. 20A and 20B are graphs showing plots of the relationship between Ti concentration in the first layer and the elongation at break.
Figure 20B:
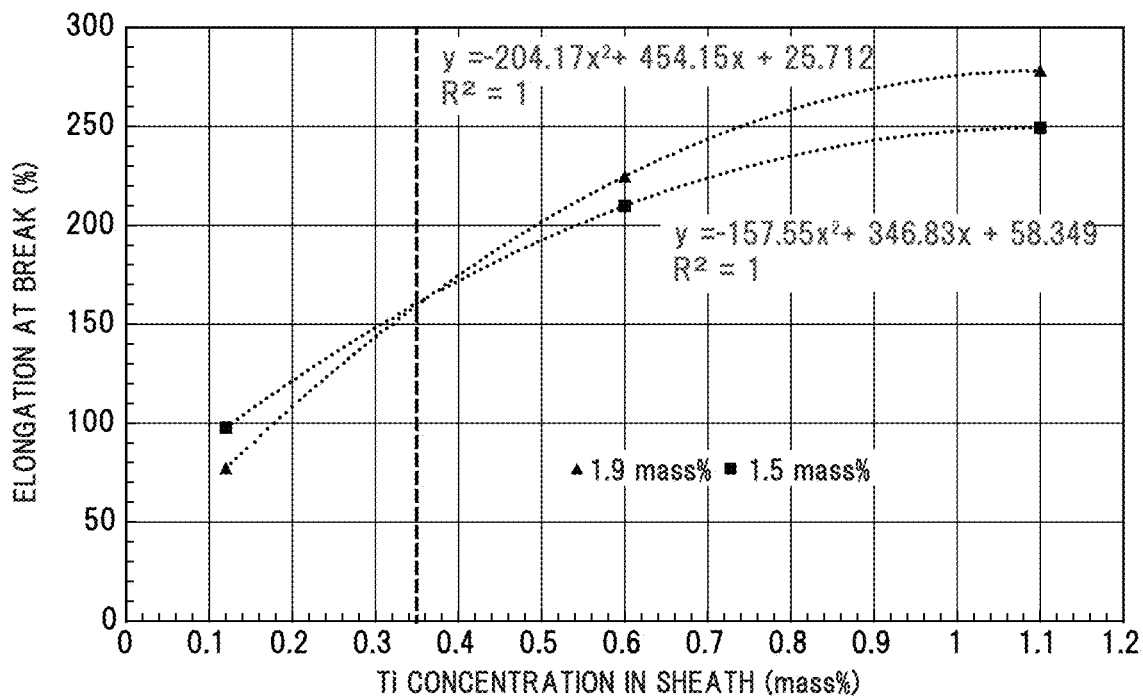

It is found from the results shown in FIGS. 18A to 18D, 19A to 19D and Table 6 that it is effective to increase the amount of TiO$_2$ fine particles in the first layer 10 in order to increase the elongation at break of the laminate structure 1. Also, as shown in FIGS. 20A and 20B, the relationship between Ti concentration (content of TiO$_2$ fine particles) in the first layer 10 and the elongation at break (result of D3, D7, D10, D4, D8, and D11) is plotted, and polynomial approximations were performed. FIG. 20A shows the result after exposure to UV-C light at 1404 J/cm$^2$. FIG. 20B shows the result after exposure to UV-C light at 2808 J/cm$^2$. It is found that the Ti concentration in the first layer 10 should be 0.4 mass % or more to ensure that the elongation at break is at least 250% even after being exposed to UV-C light of 1404 J/cm$^2$. In addition, it is found that the Ti concentration in the first layer 10 should be 0.35 mass % or more to ensure that the elongation at break is at least 150% even after being exposed to UV-C light of 2808 J/cm$^2$.

Next, a surface wipe test was performed on a sample C11 including a TiO$_2$ fine particles 113 at a concentration of 1.9 mass % in the second layer 11 as the coating film 24 and a sample including TiO$_2$ fine particles 113 at a concentration of 4.4 mass % in the second layer 11 (sample C12) which was prepared similarly to the sample C11. This sample preparation and testing for the wipe test were carried out in the same way as Japanese Patent No. 6723489. Preparation of samples for measuring the static friction coefficient before and after the wipe test and measurement were performed using the same method as for Japanese Patent No. 6723489. The ambient temperature was 25+/−3° C., the ambient humidity was 50+/−10%, and the pressure was atmospheric pressure at the wiping test site and the static friction coefficient measurement site.

In this wipe test, a long fiber non-woven fabric (with a length of 50 mm in a wipe direction) including cotton linters including disinfectant alcohol was brought contiguous to the surface of the coating film 24 at a shearing stress of 2×10$^{-3}$ MPa to 4×10$^{-3}$ MPa, and the surface of the layer was repeatedly wiped off for approximately 150 mm length in the wipe direction at a speed between 80 times/min to 120 times/min 20,000 times (for 10,000 reciprocations). As a result, a difference (in absolute values) between the static friction coefficients of the coating film 24 of the samples C11 and C12 before and after the testing was 0.019 and 0.047, i.e., both values are not greater than 0.1. Table 7 below shows the values of the static friction coefficients of the coating film 24 of the measured samples C11, C12.

TABLE 7

| | Before the wipe test | After the wipe test | The difference before and after the test (Absolute value) |
|---|---|---|---|
| C11 | 0.167 | 0.188 | 0.019 |
| C12 | 0.122 | 0.169 | 0.047 |

On the other hand, the surface condition of the samples C11 and C12 before and after the wipe test was observed by SEM, and there was a difference between the two samples.

Figure 21A:
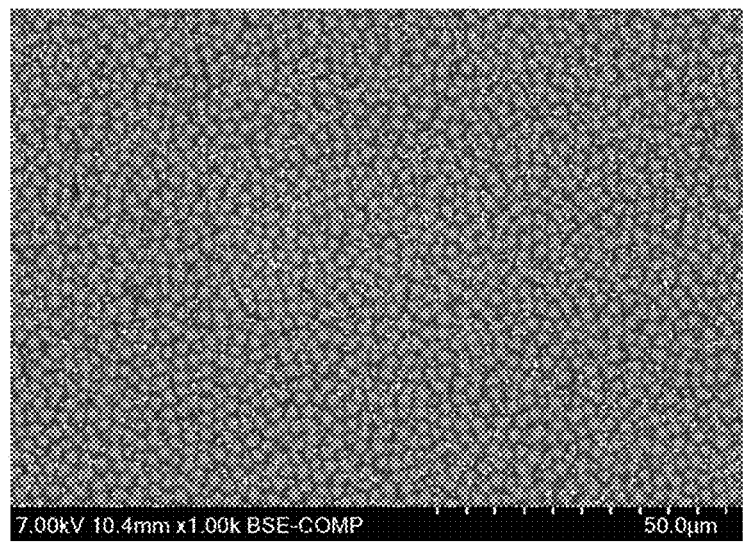
FIGS. 21A and 21B are observation images of the surfaces of sample C11 and sample C12 before the wipe test, respectively.
Figure 21B:
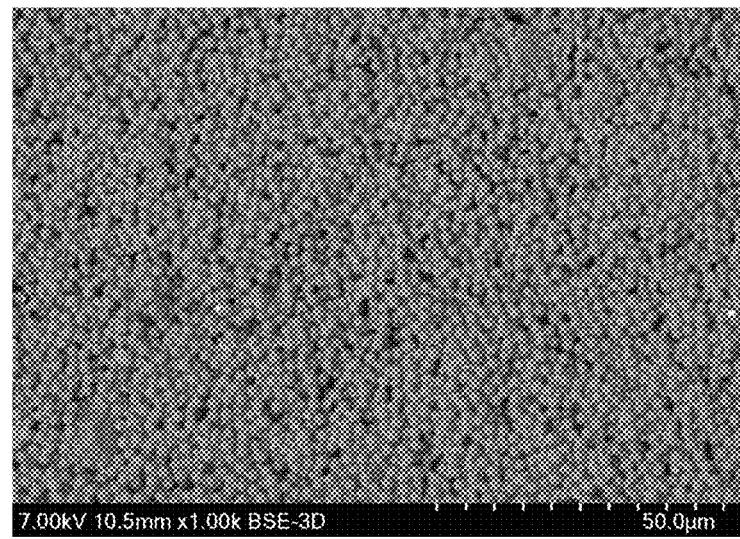
Figure 22A:
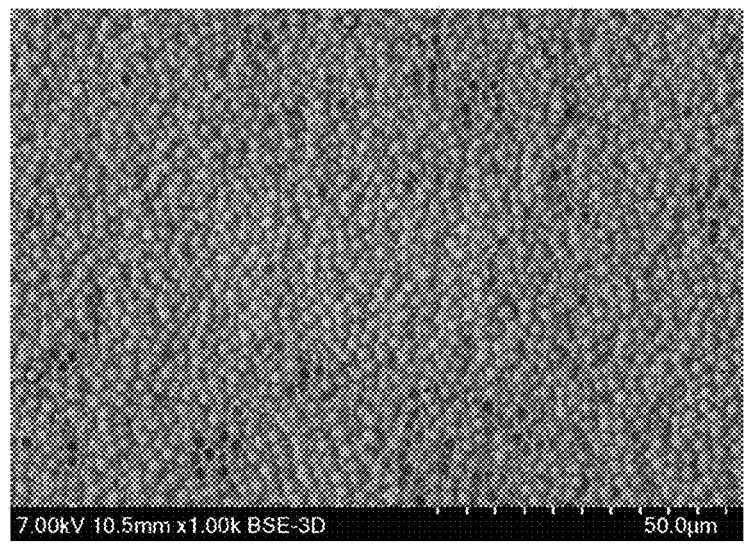
FIGS. 22A and 22B are observation images of the surfaces of sample C11 and sample C12 after the wipe test, respectively.
Figure 22B:
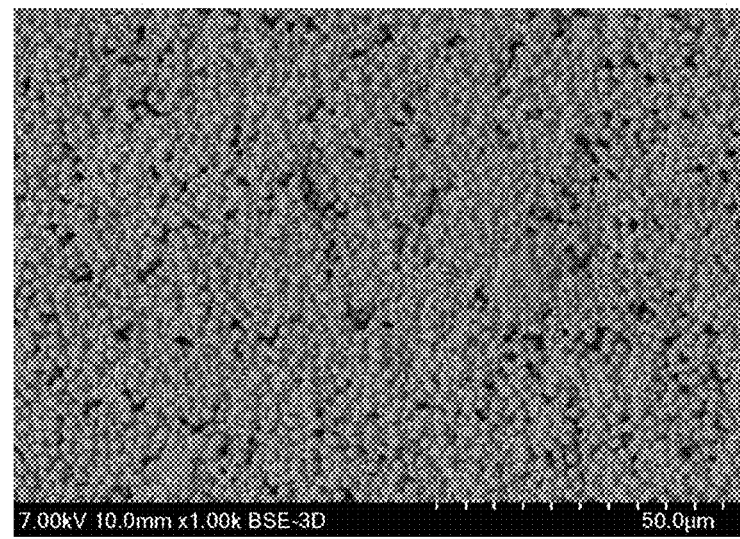

FIGS. 21A and 21B show 1000× images of the surface before the wipe test of the samples C11 and C12, respectively. FIGS. 22A and 22B show the surface observations after the wipe test of the samples C11 and C12, respectively. Spherical particles and white powder particles around the spherical particle observed in the observation images in FIGS. 21A, 21B, 22A and 22B are the fine particles 112 and TiO$_2$ fine particles 113, respectively.

As shown in FIGS. 21A and 21B, the voids were more observed in the coating film 24 of the sample C12 than in the coating film 24 of the sample C11. Also, as shown in FIGS. 22A and 22B, the drop of fine particles 112 in the coating film of the sample C12 was more than that in the coating film 24 of the sample C11. One of the major causes of these results is assumed that the concentration of TiO$_2$ fine particles 113 in the coating film 24 (second layer 11) of the sample C12 was too high. The presence of more TiO$_2$ fine particles 113 around the fine particle 112 has resulted in a smaller contact area between the base material 111 composed of the silicone rubber and the fine particle 112. This may have resulted in reduced adhesion. Based on the results of the wipe test and SEM observation, it is confirmed that the upper limit of Ti concentration in the coating film 24 is 4.4 mass %.

The preferred ranges of Ti concentrations of the first layer 10 including TiO$_2$ fine particles 102 and the second layer 11 including TiO$_2$ fine particle 113, described in the first embodiment with referring to FIG. 2 are derived from the results of tests in this example.

Summary of the Embodiment

Next, the technical thought that is understood from the embodiment described above will be described with the aid of the sign in the embodiment, etc. However, the following signs, etc., do not limit the scope of the patent claim to the members, etc. that are specifically indicated in the embodiment.

[1] A laminate structure (1) comprising: a first layer (10) as a substrate; and a second layer (11) being provided on the first layer (10) and comprising a rubber composition including a rubber component (111), first fine particles (112) for providing a surface with irregularity, and second fine particles (113) for shielding UV-C light, wherein when performing Raman mapping analysis on a first peak derived from oscillation of the second fine particles (113) in Raman scattering spectrum obtained by Raman scattering measurement of the second layer (11), the second layer (11) includes a region where an intensity of the first peak is greater in an area where the first fine particles (112) are not present than an area where the first fine particles (112) are present.

[2] The laminate structure (1) described in [1], wherein the rubber component (111) is a silicone rubber, and the first fine particles (112) comprise a material being more resistant to UV-C light than the silicone rubber and including Si.

[3] The laminate structure (1) described in [1] or [2], wherein the first fine particles (112) comprise at least one of silicone resin fine particles and silica fine particles.

[4] The laminate structure (1) described in any one of [1] to [3], wherein the second fine particles (113) comprise titanium oxide fine particles.

[5] The laminate structure (1) described in any one of [1] to [4], wherein a Ti concentration of the second layer (11) is 5 mass % or more.

[6] A cable (20) comprising: an insulator comprising the laminate structure (1) described in any one of [1] to [5].

[7] A tube (40a, 40b, 40c) comprising: an insulator comprising the laminate structure (1) described in any one of [1] to [5].

[8] A laminate structure (1) comprising: a first layer (10) comprising a silicone rubber as a base material; and a second layer (11) being provided on the first layer (10) and comprising a silicone rubber as a base material (111), first fine particles (112) for providing a surface with irregularity, and second fine particles (113) for shielding UV-C light, wherein the first fine particles (112) comprise a material being more resistant to UV-C light than the silicone rubber and including Si, and wherein an average particle size of the second fine particles (113) is ½ or less of an average particle size of the first fine particles (112).

[9] A laminate structure (1) comprising: an insulator (10, 11) comprising a silicone rubber as a base material, wherein an elongation at break measured by a tensile test after being exposed to UV-C light of 1404 J/cm$^2$ is at least 250%, wherein when observing areas each having a size of 1.5 mm×4.5 mm using an optical microscope with a 50× magnification ratio at ten locations during a bending test equivalent to 45% to 50% tensile after being exposed to the UV-C light of 1404 J/cm$^2$, a number of areas on which cracks are observed is 3 or less.

[10] A laminate structure (1) comprising: an insulator (10, 11) comprising a silicone rubber as a base material, wherein an elongation at break measured by a tensile test after being exposed to UV-C light of 2808 J/cm$^2$ is at least 150%, wherein when observing areas each having a size of 1.5 mm×4.5 mm using an optical microscope with a 50× magnification ratio at ten locations during a bending test equivalent to 45% to 50% tensile after being exposed to the UV-C light of 2808 J/cm$^2$, a number of areas on which cracks are observed is 3 or less.

[11] A laminate structure (1) comprising: a first layer (10) comprising a silicone rubber as a base material (101) and first TiO$_2$ fine particles (102); and a second layer (11) being provided on the first layer (10) and comprising a silicone rubber as a base material (111) and second TiO$_2$ fine particles (113), wherein a Ti concentration of the first layer (10) is 0.35 mass % or more and 3.0 mass % or less, and a Ti concentration of the second layer (11) is 1.0 mass % or more and 4.4 mass % or less.

[12] The laminate structure (1) described in [11], wherein the Ti concentration of the second layer (11) is higher than the Ti concentration of the first layer (10).

[13] The laminate structure (1) described in [11] or [12], wherein the second layer (11) includes at least one of silicone resin fine particles and silica fine particles.

[14] A cable (20) comprising: an insulator (23, 24) comprising the laminate structure (1) described in any one of [11] to [13].

[15] A tube (40a, 40b, 40c) comprising: an insulator comprising the laminate structure (1) described in any one of [11] to [13].

Although the embodiment and examples of the invention has been described above, the invention is not to be limited to the embodiment and examples described above, and the invention can be appropriately modified and implemented in various ways without departing from the gist thereof. In addition, the embodiment and examples described above do not limit the inventions according to claims. Further, please note that not all combinations of the features described in the embodiment and examples are necessary to solve the problem of the invention.

The invention claimed is:
1. A laminate structure comprising:
a first layer as a substrate; and
a second layer being provided on the first layer and comprising a rubber composition including a rubber component, first fine particles for providing a surface with irregularity, and second fine particles for shielding UV-C light,
wherein an average particle size of the second fine particles is smaller than an average particle size of the first fine particles,
wherein the average particle size of the first fine particles is 1 μm or more and 10 μm or less,
wherein the average particle size of the second fine particles is 10 nm or more and 1 μm or less,
wherein when performing Raman mapping analysis on a first peak derived from oscillation of the second fine particles in Raman scattering spectrum obtained by Raman scattering measurement of the second layer, the second layer includes a region where an intensity of the first peak is greater in an area where the first fine particles are not present than an area where the first fine particles are present,
wherein the first layer includes first TiO$_2$ fine particles, and the second fine particles of the second layer include TiO$_2$ fine particles, wherein a Ti concentration of the first layer is 0.35 mass % or more and 3.0 mass % or less, and a Ti concentration of the second layer is 1.0 mass % or more and 4.4 mass % or less, and wherein a Ti concentration of the second layer is higher than a Ti concentration of the first layer.

2. The laminate structure according to claim 1, wherein the rubber component is a silicone rubber, and the first fine particles comprise a material being more resistant to UV-C light than the silicone rubber and including Si.

3. The laminate structure according to claim 1, wherein the first fine particles comprise at least one of silicone resin fine particles and silica fine particles.

4. The laminate structure according to claim 1, wherein when observing areas each having a size of 1.5 mm×4.5 mm using an optical microscope with a 50× magnification ratio at ten locations during a bending test equivalent to 45% to 50% tensile after being exposed to the UV-C light of 1404 J/cm$^2$, a number of areas on which cracks are observed is 3 or less.

5. The laminate structure according to claim 1, wherein a Ti concentration of the second layer is 1.5 mass % or more.

6. A cable comprising: an insulator comprising the laminate structure according to claim 1.

7. A tube comprising: an insulator comprising the laminate structure according to claim 1.

8. The laminate structure according to claim 1, wherein the mass % of the first fine particles is between 10 mass % or more and 60 mass % or less.

9. The laminate structure according to claim 1, wherein the first fine particles comprise at least one of silicone resin fine particles and silica fine particles.

10. A laminate structure comprising:

an insulator comprising a silicone rubber first layer including first TiO$_2$ fine particles, and second layer in direct contact with the first layer and including a silicone rubber and second TiO$_2$ fine particles and first fine particles, wherein an average particle size of the second TiO$_2$ fine particles is smaller than an average particle size of the first fine particles, wherein the average particle size of the first fine particles is 1 μm or more and 10 μm or less, wherein the average particle size of the second TiO$_2$ fine particles is 10 nm or more and 1 μm or less, wherein an elongation at break measured by a tensile test after being exposed to UV-C light of 1404 J/cm$^2$, at wavelength 253.7 nm, illuminance of 1.3 mW/cm$^2$, and irradiation times of 300 hours, is at least 250%, wherein when observing areas each having a size of 1.5 mm×4.5 mm using an optical microscope with a 50× magnification ratio at ten locations during a bending test equivalent to 45% to 50% tensile after being exposed to the UV-C light of 1404 J/cm$^2$, a number of areas on which cracks are observed is 3 or less, and wherein a Ti concentration of the second layer is higher than a Ti concentration of the first layer.

11. The laminate structure according to claim 10, wherein the mass % of the first fine particles is between 10 mass % or more and 60 mass % or less.

12. The laminate structure according to claim 10, wherein the first fine particles comprise at least one of silicone resin fine particles and silica fine particles.

13. A cable comprising: an insulator comprising the laminate structure according to claim 10.

14. A tube comprising: an insulator comprising the laminate structure according to claim 10.

15. A laminate structure comprising:

a first layer comprising a silicone rubber as a base material and first TiO$_2$ fine particles; and a second layer being provided on the first layer to directly contact on the first layer and comprising a silicone rubber as a base material, first fine particles, and second TiO$_2$ fine particles, wherein a Ti concentration of the first layer is 0.35 mass % or more and 3.0 mass % or less, and a Ti concentration of the second layer is 1.0 mass % or more and 4.4 mass % or less, wherein an average particle size of the second TiO$_2$ fine particles is smaller than an average particle size of the first fine particles, wherein the average particle size of the first fine particles is 1 μm or more and 10 μm or less, wherein the average particle size of the second TiO$_2$ fine particles is 10 nm or more and 1 μm or less, and wherein the Ti concentration of the second layer is higher than the Ti concentration of the first layer.

16. The laminate structure according to claim 15, wherein the first fine particles of the second layer includes at least one of silicone resin fine particles and silica fine particles.

17. A cable comprising: an insulator comprising the laminate structure according to claim 15.

18. A tube comprising: an insulator comprising the laminate structure according to claim 15.

19. The laminate structure according to claim 15, wherein the mass % of the first fine particles is between 10 mass % or more and 60 mass % or less.

* * * * *